United States Patent
Nishimura et al.

(10) Patent No.: US 9,512,441 B2
(45) Date of Patent: Dec. 6, 2016

(54) TECHNIQUE FOR REGULATING FLOWER BUD FORMATION IN SUGARCANE

(71) Applicants: Satoru Nishimura, Nagoya (JP); Kazuyo Suzuki, Toyota (JP); Shoko Tsuzuki, Nagoya (JP)

(72) Inventors: Satoru Nishimura, Nagoya (JP); Kazuyo Suzuki, Toyota (JP); Shoko Tsuzuki, Nagoya (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 31 days.

(21) Appl. No.: 14/406,592

(22) PCT Filed: Nov. 6, 2012

(86) PCT No.: PCT/JP2012/078716
§ 371 (c)(1),
(2) Date: Dec. 9, 2014

(87) PCT Pub. No.: WO2013/190720
PCT Pub. Date: Dec. 27, 2013

(65) Prior Publication Data
US 2015/0135373 A1    May 14, 2015

(30) Foreign Application Priority Data
Jun. 21, 2012 (JP) ................ 2012-140231

(51) Int. Cl.
C12N 15/29 (2006.01)
C12N 15/82 (2006.01)
C07K 14/415 (2006.01)

(52) U.S. Cl.
CPC ........ *C12N 15/827* (2013.01); *C07K 14/415* (2013.01); *C12N 15/8225* (2013.01)

(58) Field of Classification Search
None
See application file for complete search history.

(56) References Cited

U.S. PATENT DOCUMENTS

| | | | |
|---|---|---|---|
| 2002/0029395 A1 | 3/2002 | Weigel et al. | |
| 2003/0236208 A1* | 12/2003 | Kmiec | C12N 15/102 514/44 R |
| 2004/0088763 A1 | 5/2004 | Yano et al. | |
| 2006/0272057 A1* | 11/2006 | Danilevskaya | C07K 14/415 800/287 |
| 2013/0291232 A1 | 10/2013 | Hattori et al. | |

FOREIGN PATENT DOCUMENTS

| | | |
|---|---|---|
| CN | 1487997 A | 4/2004 |
| CN | 103298829 A | 9/2013 |
| JP | 2000-139250 A | 5/2000 |
| JP | 2002-511270 A | 4/2002 |
| JP | 2002-153283 A | 5/2002 |

OTHER PUBLICATIONS

Kojima et al. (Plant Cell Physiol. 43:1096-1105(2002).*
Hanzawa et al. (PNAS, May 24, 2005 vol. 102, No. 21, 7748-7753.*
Morton et al. (The Plant Cell, vol. 26: 2746-2760, Jul. 2014).*
Guo et al. (2004, Proc. Natl. Acad. Sci. USA 101: 9205-9210).*
Igor Kardailsky et al., "Activation Tagging of the Floral Inducer FT," Science, Dec. 3, 1999, pp. 1962-1965, vol. 286, No. 5446.
Shoko Kojima et al., "Hd3a, a Rice Ortholog of the *Arabidopsis* FT Gene, Promotes Transition to Flowering Downstream of Hd1 under Short-Day Conditions," Plant Cell Physiol., Oct. 2002, pp. 1096-1105, vol. 43, No. 10.

* cited by examiner

*Primary Examiner* — Elizabeth McElwain
*Assistant Examiner* — Charles Logsdon
(74) *Attorney, Agent, or Firm* — Sughrue Mion, PLLC

(57) ABSTRACT

This invention provides a technique that enables efficient cross-breeding of plants, and, in particular, sugarcane plants and plant species closely related thereto.

6 Claims, 11 Drawing Sheets

Fig. 1

```
LOCUS
BASE COUNT       740 a    1007 c    968 g    674 t
ORIGIN
     1 ATCAAACTCG CAGCAGTAGA GCAGCACGAG CAACACGCCG CGCCGCTCCA ACCATCTCAG
    61 CTTCGCGCTT CCCGCGCCCC GCCGCCGCGC CCGCCATGGC GTCCGAGCGG CACCACTCCA
   121 TCGACGCGCA GCTCCGTGCC CTGGCCCCCG GCAAGGTCTC CGAGGAGCTC ATCCAGTACG
   181 ACGCCCTGCT CGCCGACCGT TTCCTCGACA TCCTCCAGGA CCTCCATGGC CCTAGCCTTC
   241 GCGAATTTGT CCAGGAGTGC TACGAGGTGT CGGCCGATTA CGAGGGCAAG AAGGACACGT
   301 CGAAGCTGGG CGAGCTGGGC ACCAAGCTCA CGGGGCTGGC GCCCGCCGAC GCCATCCTGG
   361 TGGCGAGCTC CATCCTGCAC ATGCTCAACC TGGCCAACCT GGCCGAGGAA GTGGAGCTGG
   421 CGCACCGCCG CCGGAACAGC AAGCTCAAGC ACGGGGACTT CTCCGACGAG GGCTCCGCCA
   481 CCACCGAGTC GGACATCGAG GAGACGCTCA AGCGCCTCGT GTCGCTGGGC AAGACCCCCG
   541 AGGAGGTGTT CGAGGCGCTC AAGAACCAGA GCGTCGACCT CGTCTTCACC GCGCACCCCA
   601 CGCAGTCCGC CAGGAGGTCG CTCCTGCAGA AAAACGCCAG GATCCGGAAT TGTCTGACGC
   661 AGCTGAGTGC CAAGGACGTC ACGGACGACG ACAAGAAGGA GCTCGACGAG GCTCTGCAGA
   721 GAGAGATCCA AGCAGCTTTC AGAACTGATG AGATCCGGAG AGCACAACCC ACCCCACAGG
   781 ATGAAATGCG CTATGGGATG AGCTACATCC ATGAAACTGT ATGGAAGGGT GTGCCTAAGT
   841 TTTTGCGCCG TGTGGATACA GCCCTGAAGA ATATCGGCAT CAATCAGCGG CTTCCCTACA
   901 ATGTTCCTCT CATTAAGTTC TGGTCTTGGA TGGGTGGTGA CCGTGATGGA AATCCAAGAG
   961 TAACTCCGGA GGTGACAAGA GAAGTATGCT TGCTGTCCAG AATGACGGCT GCAAACTTGT
  1021 ACATCGATCA GGTCGAAGAC CTGATGTTTG AGCTCTCTAT GTGGCGCTGC AATGATGAAC
  1081 TTCGTGCTCG AGCCGAAGAA GTCCAGAGTA CTCCAGCTTC AAAGAAAGTT ACCAAGTATT
  1141 ACATAGAATT CTGGAAGCAA ATTCCTCCAA ACGAGCCCTA CCGGGTGATA CTTGGTGCTG
  1201 TAAGGGACAA GTTATACAAC ACACGCGAGC GTGCACGCCA TCTGCTGGCA ACTGGATTTT
  1261 CTGAAATTTC TGTGGACTCG GTATTTACCA ATATCGAAGA GTTCCTTGAG CCCGTTGAGC
  1321 TATGCTACAA ATCCCTGTGT GACTGCCGCG ACAAGGCCAT CGCGGACGGG AGCCTCCTGG
  1381 ACCTCCTGCG CCAGGTGTTC ACGTTCGGGC TCTCCCTGGT GAAGTTGGCA ATCCGTCAGG
  1441 AGTCGGAGCG GCACACCGAC GTGATCGACG CCATCACCAC GTACCTTGGC ATCGGGTCGT
  1501 ACCGCTCGTG GCCCGAGGAC AAGCGGATGG AGTGGCTGGT GTCGGAGCTG AAAGGCAAGC
  1561 GGCCGCTGCT GCCCCCGGAC CTTCCCATGA CCGAGGAGAT CGCCGACGTC ATCGGGGCGA
  1621 TGCACGTCCT CGCGGAGCTC CCGTCGGACA GCTTCGGCCC CTACATCATC TCCATGTGCA
  1681 CAGCCCCCTC CGACGTGCTC GCCGTGGAGC TCCTGCAGCG CGAGTGTGGC ATTCGCCAGA
  1741 CGCTGCCCGT GGTGCCGCTG CTCGAGAGGC TGGCCGACCT GCAGGCGGCG CCCGCGTCCG
  1801 TGGAGCGGCT CTTCTCCACT GACTGGTACT TCGACCACAT CAAGGGCAAG CAGCAGGTGA
  1861 TGGTCGGGTA CTCCGACTCC GGCAAGGACG CCGGCCGCCT GTCCGCGGCG TGGCAGCTGT
  1921 ACGTGGCGCA GGAGGAGATG GCCAAGGTGG CCAAGAAATA CGGCGTGAAG CTGACCTTGT
  1981 TCCACGGGCG CGGCGGCACC GTGGGCAGGG GTGGCGGGCC GACGCACCTG GCCATCCTGT
  2041 CCCAGCCGCC GGACACCATC AACGGGTCAA TCCGCGTGAC GGTGCAGGGC GAGGTCATCG
  2101 AGTTCATGTT CGGGGAGGAT CACCTGTGCT TCCAGTCTCT GCAGCGCTTC ACGGCCGCCA
  2161 CGCTGGAGCA CGGGCATGCA CCGCGGGTGT CTCCCAAGCC CGAGTGGCGC AAGCTCATGG
  2221 AGGAGATGGC AGTCGTGGCC ACGGAGGAGT ACCGCTCCGT CGTCGTCAAG GAGCCGAGAT
  2281 TCGTCGAGTA CTTCAGATCG GCTACCCCTG AGACTGAGTA CGGGAAGATG AACATCGGCA
  2341 GCCGGCCAGC CAAGAGGAAG CCGGGCGGCG GCATCACCAC CCTGCGCGCC ATCCCCTGGA
  2401 TCTTCTCGTG GACCCAGACG AGGTTCCACC TCCCCGTGTG GCTGGGAGTC GGCGCCGCCT
  2461 TCAAGTGGGC CATCGACAAG GACATCAAGA ACTTCCAGAA GCTCAAAGAG ATGTACAACG
  2521 AGTGGCCATT CTTCAGGGTC ACCCTGGACC TGCTGGAGAT GGTTTTCGCC AAGGGAGATC
  2581 CTGGCATTGC CGGCTTGTAT GACTTGCTGC TTGTCGCCGA CGATCTCAAG CCCTTTGGA
  2641 AGCAGCTCAG GGACAAATAC GTGGAGACAG AGAAGCTTCT CCTACAGATC GCTGGGCACA
  2701 AGGATATTCT TGAAGGCGAT CCTTACCTGA AGCAGGGGCT GCGGCTACGC AATCCCTACA
  2761 TCACCACCCT GAACGTGTTG CAGGCCTACA CGCTGAAGCG GATAAGGGAT CCGAGCTTCA
  2821 AGGTGACGCC GCAGCCGCCG CTGTCCAAGG AGTTCGCCGA CGAGAACAAG CCCGCCGGAC
  2881 TGGTGAAGCT GAACCCGGCG AGCGAGTACC CGCCGGGCT GGAAGACACG CTCATCCTCA
  2941 CCATGAAAGG TATCGCCGGC GCATGCAGA ACACCGGCTA GGCCGCTTCC CTTCACTCAC
  3001 CTGCAGAGTA CTGCACGGCA ATAATAATCA GCTTCCGGAT GGTGTCGTTT TGTCAGTTTT
  3061 GGATGGAAAT GCTGAAAACT GACACCTTCT GTTTTCACTA TGTTTATGTT TATGTAATTT
  3121 CCTCGGCTTT GGCCTCTTTA TATTTTCACT CTTGTTGTGA AGTCCAAGTG GAAAAATCTT
  3181 GGCATCTTAA ACATATTGTA ATAATGAACA TCATACAATC TACAAATTTA CTATTTTGTA
  3241 TTAATCTATC TGGCAGGGAA AATGTCACTT TATATCCCAG CCCATTGGAT GGACTTTTTT
  3301 ACCATGATGC TAGTTCAACC ATCCTCTTTT GATTGTGCTA AACAAATTCT GAAATCAAAT
  3361 GCCTGGCAAT ATATGTTACC GGTTGAATC
```

Fig. 3

```
     HindIII
   1 AAGCTTTAGG AGATGCGGTG TGGTACTAAA TGCAAGGTCC AAATTCAATG CTTTTTCCAT
  61 GTTTCTTTGA AACGCAATGC CACATCTTTC TTTAAAGTAA GAACTGAGGG GTCCCATGTT
 121 TCTTTTTGCA CTTTTCACAA GAATGTACAA CTGAAAATAT CATGAAACAT CATTACCCTC
 181 TTTATATGCG TCGTCATCTA TTCACCTAAA CTCACTGATA GGATTGATGC ACTTCAGTAC
 241 ACTCATACGT GACAACTACT GTTTTTGAAA GTGAACATTT GTAGTGCTAC TATTTGCATG
 301 TATGGGAAAT TGGGAATTCT TTCTTGCCAT GGCTGATCCA GATCTCGACC TGCTTGATCT
 361 AATGCAAACA TGCATGTTGA TAGCAAGCTG AGGATCTAGA GATATAAGGT GTTAGGAGAT
 421 GCGGTGTGGT ACTAAATGCA AGGTCAAAAT TCCATGCTTT TTCCATGCTC AATTACCTAG
 481 CATTTCCTAA TTTTTAATTG TGATAACTAA TGCATCGAGC CATATATAAT TCAGTAAATA
 541 TGTATATTTA AGCATATATA TATATATACA GTTTACATTT CTAATTCTTC TTTTTTTGTG
 601 TGGAGGTCCG CGACGATGCA AGTTGCTCCC AACCCAAATT AATCCACCTC TCTTAAATCC
 661 GCAGATCTTC ACCACCAGCA GCTACACATC GTATTGTGTC GGCTTGACCG CATGTGCGCG
 721 CTGGGTTTTG GCAGCGCCTG AATGCAGTAC AGCCACCTGT ATGGTGCCCT TGGTAGAGTA
 781 ACACCCTTAT CCCTACGGCA GCCATGTATA ACCCTTATCC CTACGGCAGC CATGTATTGT
 841 AGCCCATCTT CTTAACCACA AGTTCATTTT AAATTTCCGG CCGGTCTCTT GAGGAAATCA
 901 AATTTTATTT TCACAATTTA TATGGATATA GGATAATCTA TGTTCCTAAC AGTGGCTAAC
 961 AGGCTCCCTC TCCTCCACAT ACATCGCGTG CAAGCATTCC TCCAAACTCT TCCGATCCCC
1021 CGAATCCAGC CTTGACTGCA AACAGACGCC CCTCTCCACA TCCTGCACAC CCATCAGCCA
1081 ACGGAATAAC AGAAGAAGGC GAGTGAGCAG TGACAAAGCA CGTCAACAGC AGCGAGCCAA
1141 GCCAAAATGG AGCCAGGAGC AAGCCGCGGC CGCAGCTCTC CCGGTCCCCC TTGCGGTTAC
1201 CGCTAGCAAA CGCCCCTCTC CACATCCTGC AACACAAGGA GGCAAGTGCG CAGTGACAAA
1261 GTACGTCCAC AGCAGCGAGC CAAGCCAAAA GGAGCTCAGC CACAGCCGCA GCTCTCGGCT
1321 ACCGTTACCG CCGATCACAT GCATGCCTTT CCAAACGCCA AGGGCCGCGC AATCCCGTGC
1381 ACACCGACCA CACACTCGCC AACTCCCCAT CCCTATTTGA AGCCACCGGC CCGCGCACTG
1441 CATTGATCAA CTCGCAGCAG TAGAGCAGCA CGAGCAACAC GCCGCGCCGC TCCAACCATC
1501 TCAGCTTCGC GCTTCCCGCG CCCCGCCGCC GCGCCCGCCA TG CCTAGG
                                         Start codon BlnI
```

```
  1 tgcaccacac acagttcagc tagcagatca cctagctaga tagctgcctc tatcacagta
 61 tatttgctcc ctgcaacttg ctgctgctgc aatagctagc agctgcagct agtaagcaaa
121 actataaacc ttcagggttt tttgcaagat cgatggccgg aagtggcagg gacagggacc
181 ctcttgtggt tggtagggtt gtgggtgatg tgctggacgc gttcgtccgg agcaccaacc
241 tcaaggtcac ctatggctcc aagaccgtgt ccaatggctg cgagctcaag ccgtccatgg
301 tcacccacca gcctagggtc gaggtcggcg gcaatgacat gaggacattc tacacccttg
361 tgatggtaga cccagatgca ccaagcccaa gtgaccctaa ccttagggag tatctacatt
421 ggttggtcac tgatattcct ggtactactg cagcgtcatt tgggcaagag gtgatgtgct
481 acgagagccc aaggccaacc atggggatcc accggctggt gttcgtgctg ttccagcagc
541 tggggcgtca gacagtgtac gcgcccgggt ggcgtcagaa cttcaacacc aaggacttcg
601 ccgagctcta caacctcggc tcgccggtcg ccgccgtcta cttcaactgc cagcgcgagg
661 caggctccgg cggcaggagg gtctacccct agctaacgat gatcccgatc gatctgctgc
721 atgctcacta tcatcatcca gcatgctata cattgcaggt tcagacaatt gaaatgattc
781 tcgacacaca acatatatat gatggtgtaa ttaattatgc aattaaatag ctgagcaagg
841 ctaaggt
```

(B)

```
  1 Met Ala Gly Ser Gly Arg Asp Arg Asp Pro Leu Val Val Gly Arg Val
 17 Val Gly Asp Val Leu Asp Ala Phe Val Arg Ser Thr Asn Leu Lys Val
 33 Thr Tyr Gly Ser Lys Thr Val Ser Asn Gly Cys Glu Leu Lys Pro Ser
 49 Met Val Thr His Gln Pro Arg Val Glu Val Gly Gly Asn Asp Met Arg
 65 Thr Phe Tyr Thr Leu Val Met Val Asp Pro Asp Ala Pro Ser Pro Ser
 81 Asp Pro Asn Leu Arg Glu Tyr Leu His Trp Leu Val Thr Asp Ile Pro
 97 Gly Thr Thr Ala Ala Ser Phe Gly Gln Glu Val Met Cys Tyr Glu Ser
113 Pro Arg Pro Thr Met Gly Ile His Arg Leu Val Phe Val Leu Phe Gln
129 Gln Leu Gly Arg Gln Thr Val Tyr Ala Pro Gly Trp Arg Gln Asn Phe
145 Asn Thr Lys Asp Phe Ala Glu Leu Tyr Asn Leu Gly Ser Pro Val Ala
161 Ala Val Tyr Phe Asn Cys Gln Arg Glu Ala Gly Ser Gly Gly Arg Arg
177 Val Tyr Pro
```

Fig. 7

```
   1 AAGCTTTAGG AGATGCGGTG TGGTACTAAA TGCAAGGTCC AAATTCAATG CTTTTTCCAT
  61 GTTTCTTTGA AACGCAATGC CACATCTTTC TTTAAAGTAA GAACTGAGGG GTCCCATGTT
 121 TCTTTTTGCA CTTTTCACAA GAATGTACAA CTGAAAATAT CATGAAACAT CATTACCCTC
 181 TTTATATGCG TCGTCATCTA TTCACCTAAA CTCACTGATA GGATTGATGC ACTTCAGTAC
 241 ACTCATACGT GACAACTACT GTTTTTGAAA GTGAACATTT GTAGTGCTAC TATTTGCATG
 301 TATGGGAAAT TGGGAATTCT TTCTTGCCAT GGCTGATCCA GATCTCGACC TGCTTGATCT
 361 AATGCAAACA TGCATGTTGA TAGCAAGCTG AGGATCTAGA GATATAAGGT GTTAGGAGAT
 421 GCGGTGTGGT ACTAAATGCA AGGTCAAAAT TCCATGCTTT TTCCATGCTC AATTACCTAG
 481 CATTTCCTAA TTTTTAATTG TGATAACTAA TGCATCGAGC CATATATAAT TCAGTAAATA
 541 TGTATATTTA AGCATATATA TATATATACA GTTTACATTT CTAATTCTTC TTTTTTTGTG
 601 TGGAGGTCCG CGACGATGCA AGTTGCTCCC AACCCAAATT AATCCACCTC TCTTAAATCC
 661 GCAGATCTTC ACCACCAGCA GCTACACATC GTATTGTGTC GGCTTGACCG CATGTGCGCG
 721 CTGGGTTTTG GCAGCGCCTG AATGCAGTAC AGCCACCTGT ATGGTGCCCT TGGTAGAGTA
 781 ACACCCTTAT CCCTACGGCA GCCATGTATA ACCCTTATCC CTACGGCAGC CATGTATTGT
 841 AGCCCATCTT CTTAACCACA AGTTCATTTT AAATTTCCGG CCGGTCTCTT GAGGAAATCA
 901 AATTTTATTT TCACAATTTA TATGGATATA GGATAATCTA TGTTCCTAAC AGTGGCTAAC
 961 AGGCTCCCTC TCCTCCACAT ACATCGCGTG CAAGCATTCC TCCAAACTCT TCCGATCCCC
1021 CGAATCCAGC CTTGACTGCA AACAGACGCC CCTCTCCACA TCCTGCACAC CCATCAGCCA
1081 ACGGAATAAC AGAAGAAGGC GAGTGAGCAG TGACAAAGCA CGTCAACAGC AGCGAGCCAA
1141 GCCAAAATGG AGCCAGGAGC AAGCCGCGGC CGCAGCTCTC CCGGTCCCCC TTGCGGTTAC
1201 CGCTAGCAAA CGCCCCTCTC CACATCCTGC AACACAAGGA GGCAAGTGCG CAGTGACAAA
1261 GTACGTCCAC AGCAGCGAGC CAAGCCAAAA GGAGCTCAGC CACAGCCGCA GCTCTCGGCT
1321 ACCGTTACCG CCGATCACAT GCATGCCTTT CCAAACGCCA AGGGCCGCGC AATCCCGTGC
1381 ACACCGACCA CACACTCGCC AACTCCCCAT CCCTATTTGA AGCCACCGGC CCGCGCACTG
1441 CATTGATCAA CTCGCAGCAG TAGAGCAGCA CGAGCAACAC GCCGCGCCGC TCCAACCATC
1501 TCAGCTTCGC GCTTCCGCGC CCCGCCGCC GCGCCCGCCa tggccggaag tggcagggac
1561 agggaccctc ttgtggttgg tagggttgtg ggtgatgtgc tggacgcgtt cgtccggagc
1621 accaacctca aggtcaccta tggctccaag accgtgtcca atggctgcga gctcaagccg
1681 tccatggtca cccaccagcc tagggtcgag gtcggcggca atgacatgag gacattctac
1741 acccttgtga tggtagaccc agatgcacca agcccaagtg accctaacct tagggagtat
1801 ctacattggt tggtcactga tattcctggt actactgcag cgtcatttgg gcaagaggtg
1861 atgtgctacg agagcccaag gccaaccatg gggatccacc ggctggtgtt cgtgctgttc
1921 cagcagctgg ggcgtcagac agtgtacgcg cccgggtggc gtcagaactt caacaccaag
1981 gacttcgccg agctctacaa cctcggctcg ccggtcgccg ccgtctactt caactgccag
2041 cgcgaggcag gctccggcgg caggagggtc taccoctag
```

TECHNIQUE FOR REGULATING FLOWER BUD FORMATION IN SUGARCANE

CROSS REFERENCE TO RELATED APPLICATIONS

This is a National Stage of International Application No. PCT/JP2012/078716 filed Nov. 6, 2012, claiming priority based on Japanese Patent Application No. 2012-140231 filed Jun. 21, 2012, the contents of all of which are incorporated herein by reference in their entirety.

TECHNICAL FIELD

The present invention relates to DNA comprising gene-expression-regulating DNA having activity of promoting gene expression specifically in mature leaves and a flower-bud-formation-inducing gene and having functions of promoting flower bud formation or ear emergence and/or branching of a plant. Also, the present invention relates to the use of such DNA.

BACKGROUND ART

Sugarcane is grown over an area totaling about 20,000,000 hectares in Brazil, India, and other regions, and it is a resource plant used for sugar production and ethanol production. Through the popularization of biofuels in the future, continuous growth of demand for sugarcane is anticipated, and enhanced production thereof is accordingly expected.

With the aim of inexpensive and stable provision of sugarcane plants as starting materials, sugarcane variety improvement and breeding have been actively attempted. To date, sugarcane variety improvement and breeding have been performed via cross-breading (Non-Patent Document 1).

However, sugarcane plants have roots in the tropics, and ear emergence and flowering are impossible in Japan, most of which lies in the "temperate zone." In addition, due to genomic structural complexity, it has been very difficult to achieve effective variety improvement and breeding.

In the past, cross-breeding was carried out between plant species determined based on experience or intuition, and many progeny plants were extensively evaluated and selected. In order to perform crossing, in general, a process of induction of flower-bud formation, flowering, pollination, promotion of fruition, and seed production is necessary. In the case of sugarcane, this process can be implemented only once a year even in a field that is suitable for growth. Thus, development of a single plant variety was very time consuming.

In addition, it was very difficult to perform crossing as desired in cases in which plant varieties to be subjected to crossing had difficulty of flowering or in cases in which the flowering time of a plant variety was different from that of another plant variety.

Accordingly, there had been a strong demand for development of a method for efficient cross-breeding of sugarcane in the art.

It has been heretofore reported that flower bud formation (ear emergence) had been induced through overexpression of flower-bud-formation-inducing genes, such as FT or OsHd3a genes, in *Arabidopsis thaliana* or *Oryza sativa* (Patent Documents 1 to 3; and Non-Patent Documents 2 and 3). In addition, the FT or OsHd3a genes have been found to exert similar effects in many other plant species.

Unfortunately, there has been no report concerning recombinant sugarcanes overexpressing the genes as described above.

PRIOR ART DOCUMENTS

Patent Documents

Patent Document 1: JP 2000-139250 A
Patent Document 2: JP 2002-511270 A
Patent Document 3: JP 2002-153283 A

Non-Patent Documents

Non-Patent Document 1: Kiyomatsu Miyasato, "*Satoukibi to sono saibai*" ("Sugarcane and Cultivation thereof"), 1986, Nihon Bummitsuto Kogyokai
Non-Patent Document 2: Kardailsky, I. et al., Science, Dec. 3, 1999; 286 (5446): 1962-1965
Non-Patent Document 3: Kojima, S. et al., Plant Cell Physiol., October 2002; 43 (10): 1096-1105

SUMMARY OF THE INVENTION

Object to be Attained by the Invention

It is an object of the present invention to provide a technique that enables efficient cross-breeding of plants, and, in particular, sugarcane plants and plant species closely related thereto.

Means for Attaining the Object

The present inventors have conducted concentrated studies in order to attain the above object. As a result, they discovered that flower bud formation (ear emergence) could be promoted in plants and interfertile plants could be efficiently obtained by expressing a flower-bud-formation-inducing gene under the regulation of gene-expression-regulating DNA having activity of promoting gene expression specifically in mature leaves. This has led to the completion of the present invention.

Specifically, the present invention encompasses the following features [1] to [5].

[1] DNA comprising any one of DNAs (a) to (d) below:
(a) DNA consisting of the nucleotide sequence as shown in SEQ ID NO: 1;
(b) DNA consisting of a nucleotide sequence that has deletion, substitution, addition, or insertion of 1 or a plurality of nucleotides in the nucleotide sequence as shown in SEQ ID NO: 1 and having activity of promoting gene expression specifically in mature leaves;
(c) DNA consisting of a nucleotide sequence having 90% or higher sequence identity with the nucleotide sequence as shown in SEQ ID NO: 1 and having activity of promoting gene expression specifically in mature leaves; and
(d) DNA hybridizing under stringent conditions to DNA consisting of a sequence complementary to the nucleotide sequence as shown in SEQ ID NO: 1 and having activity of promoting gene expression specifically in mature leaves and
DNA encoding any one of polypeptides (e) to (g) below:
(e) a polypeptide consisting of the amino acid sequence as shown in SEQ ID NO: 7;
(f) a polypeptide consisting of an amino acid sequence that has deletion, substitution, addition, or insertion of 1 or a plurality of amino acids in the amino acid sequence as shown in SEQ ID NO: 7 and having activity of promoting flower bud formation or ear emergence; and (g) a polypeptide consisting of an amino acid sequence having 90% or higher sequence identity with the amino acid sequence as shown in SEQ ID NO: 7 and having activity of promoting flower bud formation or ear emergence, wherein the DNA has a function of promoting flower bud formation or ear emergence and/or branching of a plant.

[2] A recombinant vector comprising the DNA according to [1].

[3] A transformed plant into which the DNA according to [1] or the recombinant vector according to [2] is introduced.

[4] The transformed plant according to [3], which belongs to the family Gramineae.

[5] The transformed plant according to [4], which belongs to the genus *Saccharum, Sorghum,* or *Miscanthus*.

This description includes part or all of the content as disclosed in the description and/or drawings of Japanese Patent Application No. 2012-140231, which is a priority document of the present application.

Effects of the Invention

The present invention can provide a technique that enables efficient cross-breeding of plants, and, in particular, sugarcane plants and plant species closely related thereto.

BRIEF DESCRIPTION OF THE DRAWINGS

FIG. 1 shows the nucleotide sequence (SEQ ID NO: 4) of ecc0002 EST derived from *Saccharum officinarum* (searched for using the DFCI Sugarcane Gene Index).

FIG. 3 shows the nucleotide sequence (SEQ ID NO: 5) of the gene expression regulatory region of the ecc0002 gene into which an HindIII restriction enzyme recognition sequence and a BlnI restriction enzyme recognition sequence were inserted at the 5'- and 3'-terminus, respectively.

FIG. 4(A) shows the nucleotide sequence (CDS: 153-692) (SEQ ID NO: 6) of the Hd3a gene derived from the *Oryza sativa* Japonica group, and FIG. 4(B) shows the amino acid sequence (SEQ ID NO: 7) of a polypeptide encoded by such gene.

FIG. 7 shows the nucleotide sequence (SEQ ID NO: 3) of DNA comprising expression regulatory DNA of the ecc0002 gene and the rice Hd3a gene inserted into a gene expression vector; wherein an uppercase letter represents expression regulatory DNA of the ecc0002 gene and a lowercase letter represents the rice Hd3a gene.

EMBODIMENTS FOR CARRYING OUT THE INVENTION

Figure 2:
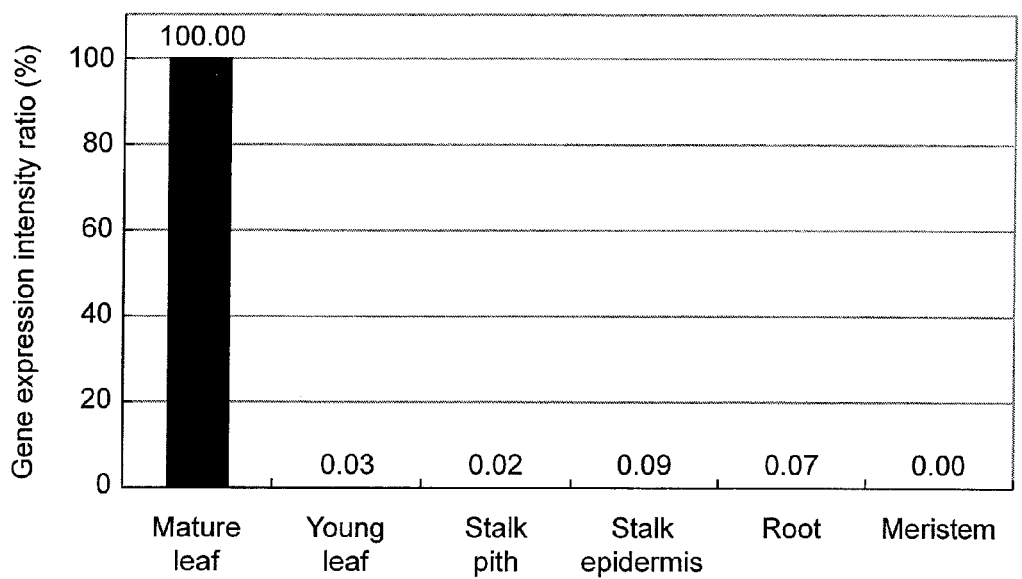
FIG. 2 shows the results of ecc0002 EST expression level analysis for individual tissues of *Saccharum* spp. cv. NiF8. The highest expression level confirmed for mature leaves is designated as 100%.

Hereafter, the present invention is described in detail.

DNA according to the present invention that has a function of promoting flower bud formation or ear emergence and/or branching of a plant comprises gene-expression-regulating DNA having activity of promoting gene expression specifically in mature leaves and a flower-bud-formation-inducing gene.

In the present invention, a function of "promoting flower bud formation or ear emergence of a plant" is a function of promoting differentiation and/or formation of flower buds or flower organs or a function of promoting ear emergence and/or flowering of a plant into which DNA having such function has been introduced (i.e., a function of shortening the period up to ear emergence and/or flowering).

In the present invention, a function of "promoting branching of a plant" is a function of promoting formation of side branches from a point in the vicinity of the base, shortening the period up to the initiation of side branch formation, and/or increasing the number of side branches of a plant into which DNA having such function has been introduced.

At the outset, gene-expression-regulating DNA having activity of promoting gene expression specifically in mature leaves is described. Hereafter, the term "gene-expression-regulating DNA having activity of promoting gene expression specifically in mature leaves" is also referred to as "gene expression regulatory DNA," and these terms are interchangeably used herein.

Gene expression regulatory DNA according to the present invention comprises any one of DNAs (a) to (d) below:

(a) DNA consisting of the nucleotide sequence as shown in SEQ ID NO: 1;

(b) DNA consisting of a nucleotide sequence that has deletion, substitution, addition, or insertion of one or a plurality of nucleotides in the nucleotide sequence as shown in SEQ ID NO: 1 and having activity of promoting gene expression specifically in mature leaves;

(c) DNA consisting of a nucleotide sequence having 90% or higher sequence identity with the nucleotide sequence as shown in SEQ ID NO: 1 and having activity of promoting gene expression specifically in mature leaves; and (d) DNA hybridizing under stringent conditions to DNA consisting of a sequence complementary to the nucleotide sequence as shown in SEQ ID NO: 1 and having activity of promoting gene expression specifically in mature leaves.

The gene expression regulatory DNA of the present invention can be obtained in the following manner: candidate genes expressed specifically in mature leaves are obtained by gene expression analysis using total RNAs derived from individual sugarcane tissues (of stalks, mature leaves, young leaves, and the like) or cDNAs derived from such RNAs; expression characteristics of the candidate genes are evaluated; genes evaluated as being expressed in a mature-leaf specific manner are specified based on the evaluation results; and the nucleotide sequence of the 5' upstream region of each candidate gene is identified based on cDNA or genomic DNA of the relevant specified gene. Here, gene expression analysis can be carried out using thorough gene expression analysis techniques known to a person skilled in the art, such as a DNA chip and a differential display method.

Specifically, the nucleotide sequence of SEQ ID NO: 1 exists in the 5' upstream region of the gene (hereinafter referred to as "ecc0002") which is specifically expressed in sugarcane mature leaves. Examples of "sugarcane" plants described herein include, but are not particularly limited to, plants belonging to the genus *Saccharum*, such as *Saccharum officinarum*, *Saccharum sinense*, *Saccharum barberi*, *Saccharum robustum*, *Saccharum spontaneum*, *Saccharum edule*, and *Saccharum* spp. hybrids cv. NiF8; and plants belonging to a genus/species closely related to the genus *Saccharum* species, such as *Sorghum*, with *Saccharum* spp. hybrids cv. NiF8 being preferable.

DNA in the 5' upstream region can be isolated by a method known to a person skilled in the art without particular limitation. For example, DNA can be isolated by a conventional technique comprising cloning an unknown region, which is the 5' upstream region herein, based on the nucleotide sequence (SEQ ID NO: 4) of the ecc0002 gene. In such a method, genomic DNA containing the 5' upstream region of the ecc0002 gene is subjected to restriction enzyme treatment such that an adopter consisting of a predetermined nucleotide sequence is ligated to the DNA. Primers are designated for the nucleotide sequence of the ecc0002 gene and the adapter, followed by PCR. Accordingly, an unknown nucleotide sequence adjacent to the 5' upstream region of the nucleotide sequence of the ecc0002 gene can be amplified. After the amplified nucleotide sequence is determined, another pair of primers is designed based on the determined nucleotide sequence. Thus, another unknown nucleotide sequence adjacent to the determined nucleotide sequence can be amplified in a similar manner. This method can be carried out using a commercially available cloning kit such as a RightWalk® kit (BEX Co., Ltd.). In addition, an inverse-PCR-based method can be implemented. In such case, a pair of primers is designed based on the nucleotide sequence information of the ecc0002 gene. PCR is performed using the pair of primers and a genomic DNA fragment obtained via treatment with a certain restriction enzyme and self-ligation. Thus, the upstream region of the ecc0002 gene can be amplified. Further, another method for isolating the upstream region of the ecc0002 gene from a genomic DNA library can be suggested. In such case, a genomic DNA library that has been prepared in accordance with a conventional technique is screened with the use of cDNA comprising the ecc0002 gene as a probe to obtain genomic DNA comprising the ecc0002 gene. Then, the nucleotide sequence of genomic DNA obtained by screening is determined. Accordingly, the 5' upstream region present in the upstream region of the ecc0002 gene can be specified. Further, the 5' upstream region can be selectively amplified by PCR or other means.

As described above, unknown nucleotide sequences located upstream of the ecc0002 gene are sequentially amplified or screened for to determine the nucleotide sequence in accordance with a conventional technique. Accordingly, the nucleotide sequence as shown in SEQ ID NO: 1 can be specified. Once the nucleotide sequence as shown in SEQ ID NO: 1 is determined, it becomes possible to obtain the nucleotide sequence as shown in SEQ ID NO: 1 by PCR using genomic DNA extracted from sugarcane as a template and primers designed based on the nucleotide sequence as shown in SEQ ID NO: 1.

The nucleotide sequence as shown in SEQ ID NO: 1 functions as a gene expression regulatory region capable of inducing gene expression specifically in mature leaves. A gene expression regulatory region contains nucleotide sequences involved in gene transcription control, such as, a promoter region, an enhancer region, a TATA box, and/or a CAT box (although the contents of the region are not particularly limited thereto).

The term "specifically" used herein refers to the following conditions: a gene expression inducible function is exclusively present in mature leaf tissue among various types of tissues constituting a plant; and the gene expression inducible function in mature leaf tissue is remarkably or statistically significantly greater (e.g., about 2, 3, 4, 5, 6, 7, 8, 9, 10, or more times greater) than the gene expression inducible function in tissues other than the mature leaf tissue (e.g., a young leaf, stalk pith, stalk epidermis, root, or meristem tissue).

The term "mature leaf" used herein refers to a leaf that contains chloroplasts accumulating in cells for photosynthesis and thus has a green tinge. It also refers to a leaf other than a young leaf containing no chloroplasts for photosynthesis.

A gene expression inducible function can be confirmed by reporter assay or other means known to a person skilled in the art. Upon reporter assay, a vector is prepared in which various reporter genes (e.g., the β-glucuronidase gene (GUS), the luciferase gene (LUC), and the green fluorescent protein gene (GFP) are ligated to the downstream region of a nucleotide sequence to be examined in terms of the gene expression inducible function. Gene introduction (or transient gene introduction) into the genome of a host is carried out using the vector. Then, the expression level of each reporter gene is determined. Thus, the gene expression inducible function can be confirmed. The reporter gene is not particularly limited, provided that the expression thereof is detectable. Examples of such reporter gene include reporter genes conventionally used by a person skilled in the art such as the CAT gene, the lacZ gene, the luciferase (hereafter denoted by "LUC") gene, the β-glucuronidase (hereafter denoted by "GUS") gene, and the green fluorescent protein (hereafter denoted by "GFP") gene.

The reporter gene expression level can be determined by a method known to a person skilled in the art, depending on reporter gene type. When the reporter gene is the CAT gene, for example, the reporter gene expression level can be determined by detecting acetylation of chloramphenicol with the gene product. The reporter gene expression level can be determined by the following technique. When the reporter gene is the lacZ gene, color development of a dye compound induced by the catalytic action of the gene expression product is detected. When the reporter gene is the LUC gene, fluorescence emission from a fluorescent compound induced by the catalytic action of the gene expression product is detected. When the reporter gene is the GFP gene, fluorescence emission from the GFP protein is detected. When the reporter gene is GUS, for example, GUS activity is determined to be promoter activity in a host cell in accordance with: (i) a method involving histochemical GUS staining (EMBO J. 6, 3901-3907, 1987) and/or (ii) the method of Castle & Morris involving the use of a fluorescent substrate (Plant Molecular Biology Manual, B5, 1-16, 1994; S. B. Gelvin & R. A. Schilperoort, Kluwer Academic Publishers). Further, the amount of the protein is determined by the method of Bradford (Anal. Biochem. 72, 248-254, 1976), and GUS activity is converted based on the amount of the protein into units of nmole 4-MU/min/mg protein. Thus, the gene expression inducible function can be confirmed.

When a gene other than the above is used as a reporter gene, in addition, the gene transcription level is determined by Northern hybridization, RT-PCR, DNA array technology, or other means. Alternatively, the expression level of the protein encoded by the gene is determined by electrophoresis such as SDS-PAGE, Western blotting, or other means.

The gene expression regulatory DNA of the present invention is not limited to the nucleotide sequence as shown in SEQ ID NO: 1. As described in (b) above, it may be a nucleotide sequence that has deletion, substitution, addition, or insertion of one or a plurality of nucleotides in the nucleotide sequence as shown in SEQ ID NO: 1, provided that it has activity of promoting gene expression specifically in mature leaves.

For example, even a nucleotide sequence that has a deletion, a substitution, an addition, or an insertion of 1 to 100 nucleotides, preferably 1 to 50 nucleotides, and more preferably 1 to 10 nucleotides in the nucleotide sequence as shown in SEQ ID NO: 1 is included in the gene expression regulatory DNA of the present invention, provided that it exhibits activity of promoting gene expression specifically in mature leaves.

In addition, the gene expression regulatory DNA of the present invention is not limited to DNA consisting of the nucleotide sequence as shown in SEQ ID NO: 1. As described in (c) above, it may be a nucleotide sequence having 80% or higher, more preferably 90% or higher, further preferably 95% or higher, and most preferably 99% or higher sequence identity to the nucleotide sequence as shown in SEQ ID NO: 1, provided that it exhibits activity of promoting gene expression specifically in mature leaves. Nucleotide sequences can be compared in accordance with a conventional technique. Comparison can be performed using, for example, BLAST® (Basic Local Alignment Search Tool of the National Center for Biological Information in the U.S.A.) on default setting.

Further, the gene expression regulatory DNA of the present invention is not limited to DNA consisting of the nucleotide sequence as shown in SEQ ID NO: 1. As described in (d) above, it may be a nucleotide sequence hybridizing under stringent conditions to DNA consisting of a sequence complementary to the nucleotide sequence as shown in SEQ ID NO: 1, provided that it exhibits activity of promoting gene expression specifically in mature leaves.

Under "stringent conditions" according to the present invention, a so-called specific hybrid is formed, but a non-specific hybrid is not formed. For example, hybridization is carried out in a solution containing 2-6×SSC (1×SSC composition: 0.15M NaCl, 0.015M sodium citrate, pH 7.0) and 0.1% to 0.5% SDS at 42° C. to 55° C., and washing is carried out in a solution containing 0.1 to 0.2×SSC and 0.1% to 0.5% SDS at 55° C. to 65° C.

Moreover, the gene expression regulatory DNA of the present invention may be a DNA fragment that has deletion of 100, 200, 300, 400, 500, 600, 700, 800, 900, 1000, 1100, 1200, 1300, 1400, 1500 or more consecutive nucleotides from the 5'-terminus and/or 3'-terminus in the nucleotide sequence as shown in SEQ ID NO: 1, provided that it exhibits activity of promoting gene expression specifically in mature leaves. Nucleotides can be deleted by a method known to a person skilled in the art (e.g., PCR or restriction enzyme treatment). The DNA fragment may be a promoter region of the gene expression regulatory DNA of the present invention. A promoter region of a predetermined gene expression regulatory DNA can be searched for using a promoter analysis tool known to a person skilled in the art (e.g., BioInformatics and Molecular Analysis Section (www-bimas.cit.nih.gov/molbio/proscan/); Prestridge, D. S., 1995, Predicting Pol II Promoter Sequences Using Transcription Factor Binding Sites, J. Mol. Biol. 249: 923-32). An example of such fragment of the nucleotide sequence as shown in SEQ ID NO: 1 is a DNA consisting of the 869th to 1119th nucleotides of the sequence as shown in SEQ ID NO: 1. The gene expression inducible function of the obtained fragment can be investigated via the above reporter assay or other means.

Once the nucleotide sequence of the gene expression regulatory DNA of the present invention is determined, it becomes possible to obtain the gene expression regulatory DNA of the present invention by chemical synthesis, PCR using genomic DNA as a template, or hybridization using a DNA fragment having the nucleotide sequence as a probe. In addition, a nucleotide sequence that has a mutation in the nucleotide sequence as shown in SEQ ID NO: 1 can be synthesized by site-directed mutagenesis or other means. Mutation can be introduced into the nucleotide sequence as shown in SEQ ID NO: 1 by a conventional technique, such as the Kunkel method or the Gapped duplex method, or a technique in accordance therewith. For example, mutation can be introduced with the use of a mutagenesis kit using site-directed mutagenesis (e.g., Mutant-K or Mutant-G (TAKARA Bio)) or a LA PCR in vitro Mutagenesis series kit (TAKARA Bio).

Subsequently, the flower-bud-formation-inducing gene is described.

The term "flower-bud-formation-inducing gene" used herein refers to a gene that encodes a protein having activity of promoting flower bud formation or ear emergence of a plant and is associated with flower bud formation or ear emergence of a plant.

Flower-bud-formation-inducing genes are known, and such genes have already been identified as the FT gene or the OsHd3a gene in *Arabidopsis thaliana* or *Oryza sativa* (JP 2000-139250 A, JP 2002-511270 A, JP 2002-153283 A, Kardailsky, I. et al., as above, Kojima, S. et al., as above). These genes can be used in the present invention. Flower-bud-formation-inducing genes can be searched for from databases available to the public (e.g., GenBank). For example, the nucleotide sequence of the Hd3a gene derived from the *Oryza sativa* Japonica group (FIG. 4, SEQ ID NO: 6) and the amino acid sequence thereof (FIG. 4, SEQ ID NO: 7) are registered under the accession number AB052944.1 with the GenBank.

Flower-bud-formation-inducing genes can be obtained by a cloning technique that is well known in the field of molecular biology. For example, a plant-derived genome library or a cDNA library can be screened with the use of probes or primers designed based on known gene sequences (e.g., the sequence registered under the accession number AB052944.1 with GenBank). A gene derived from a plant with unknown sequence information can be obtained by screening of a genomic library or a cDNA library derived from the plant with the use of probes or primers designed with the utilization of a plant gene with a known sequence. Upon sequence isolation, DNA is amplified by a standard amplification technique, such as polymerase chain reaction (PCR), and the genes (DNAs) can be obtained in amounts suitable for transformation (i.e., gene transfer).

Preferably, the flower-bud-formation-inducing gene comprises DNA that encodes a polypeptide selected from among the polypeptides (e) to (g) below:

(e) a polypeptide consisting of the amino acid sequence as shown in SEQ ID NO: 7;

(f) a polypeptide consisting of an amino acid sequence that has deletion, substitution, addition, or insertion of 1 or a plurality of amino acids in the amino acid sequence as shown in SEQ ID NO: 7 and having activity of promoting flower bud formation or ear emergence; and (g) a polypeptide consisting of an amino acid sequence having 90% or higher sequence identity with the amino acid sequence as shown in SEQ ID NO: 7 and having activity of promoting flower bud formation or ear emergence.

The amino acid sequence as shown in SEQ ID NO: 7 is an amino acid sequence of the Hd3a protein derived from rice.

In the present invention, a polypeptide encoded by the flower-bud-formation-inducing gene is not limited to a polypeptide consisting of the amino acid sequence as shown in SEQ ID NO: 7. As described in (f) above, such polypeptide may consist of an amino acid sequence that has deletion, substitution, addition, or insertion of 1 or a plurality of amino acids in the amino acid sequence as shown in SEQ ID NO: 7 and have activity of promoting flower bud formation or ear emergence.

For example, an amino acid sequence that has deletion, substitution, addition, or insertion of 1 to 20, preferably 1 to 10, and more preferably 1 to 5 amino acids in the amino acid sequence as shown in SEQ ID NO: 7 may be used in the present invention, provided that it has activity of promoting flower-bud formation.

In the present invention, a polypeptide encoded by the flower-bud-formation-inducing gene is not limited to a polypeptide consisting of the amino acid sequence as shown in SEQ ID NO: 7. As described in (g) above, it may be an amino acid sequence having 80% or higher, more preferably 90% or higher, further preferably 95% or higher, and most preferably 99% or higher sequence identity to the amino acid sequence as shown in SEQ ID NO: 7, provided that it has activity of promoting flower-bud formation. Nucleotide sequences can be compared using, for example, BLAST® on default setting, as described above.

An example of such flower-bud-formation-inducing gene is DNA consisting of the nucleotide sequence as shown in SEQ ID NO: 2. DNA consisting of the nucleotide sequence as shown in SEQ ID NO: 2 encodes the rice-derived Hd3a protein.

The flower-bud-formation-inducing gene according to the present invention is not limited to a gene consisting of the nucleotide sequence as shown in SEQ ID NO: 2. Such gene may be a gene consisting of a nucleotide sequence that has deletion, substitution, addition, or insertion of 1 or a plurality of nucleotides in the nucleotide sequence as shown in SEQ ID NO: 2, provided that it encodes a protein having activity of promoting flower bud formation or ear emergence.

For example, a nucleotide sequence that has deletion, substitution, addition, or insertion of 1 to 50 nucleotides, and preferably 1 to 10 nucleotides in the nucleotide sequence as shown in SEQ ID NO: 2 can be used in the present invention, provided that it encodes a protein having activity of promoting flower-bud formation.

The flower-bud-formation-inducing gene according to the present invention is not limited to a gene consisting of the nucleotide sequence as shown in SEQ ID NO: 2. It may be a nucleotide sequence having 80% or higher, more preferably 90% or higher, further preferably 95% or higher, and most preferably 99% or higher sequence identity to the nucleotide sequence as shown in SEQ ID NO: 2, provided that it encodes a protein having activity of promoting flower bud formation or ear emergence. Nucleotide sequences can be compared using, for example, BLAST® on default setting, as described above.

Also, the flower-bud-formation-inducing gene according to the present invention is not limited to a gene consisting of the nucleotide sequence as shown in SEQ ID NO: 2. As long as it encodes a protein having activity of promoting flower bud formation or ear emergence, it may be a nucleotide sequence hybridizing under stringent conditions to DNA consisting of a sequence complementary to the nucleotide sequence as shown in SEQ ID NO: 2.

The "stringent conditions" are as described above.

Subsequently, a recombinant vector comprising the gene expression regulatory DNA and the flower-bud-formation-inducing gene is described.

The recombinant vector of the present invention can be constructed by introducing DNA comprising the flower-bud-formation-inducing gene operably ligated to the above gene expression regulatory DNA into an appropriate vector. The term "operably ligated" used herein refers to conditions in which the above vector contains the gene expression regulatory DNA and the flower-bud-formation-inducing gene ligated to each other, so that the flower-bud-formation-inducing gene is correctly expressed under the regulation of the gene expression regulatory DNA in a host cell transfected with the above vector. The gene expression regulatory DNA and the flower-bud-formation-inducing gene may be "ligated" to each other directly or indirectly via a spacer with an adequate length and an adequate sequence. Preferably, the gene expression regulatory DNA is ligated to the flower-bud-formation-inducing gene with the use of "ATG" located at the 3'-terminus of the nucleotide sequence as shown in SEQ ID NO: 1 as "ATG" encoding the first methionine of the flower-bud-formation-inducing gene. An example of such DNA includes a DNA consisting of the nucleotide sequence as shown in SEQ ID NO: 3 in which the gene expression regulatory DNA is ligated to the flower-bud-formation-inducing gene with the use of "ATG" located at the 3'-terminus of the nucleotide sequence as shown in SEQ ID NO: 1 as "ATG" located at the 5'-terminus of SEQ ID NO: 2.

Examples of vectors that can be preferably used in the present invention include pBI vectors, pBII vectors, pPZP vectors (Hajdukiewicz, P., Svab, Z., Maliga, P.: The small, versatile pPZP family of *Agrobacterium* binary vectors for plant transformation, Plant Mol. Biol., 25: 989-94, 1994), pCAMBIA vectors (www.cambia.org/main/r_et_cam-vec.htm), and pSMA vectors by which a functional gene can be introduced into a plant using *Agrobacterium*. Use of pBI and pBII binary vectors or intermediate vectors is particularly preferable, and examples thereof include pBI1221, pBI121, pBI101, pBI101.2, pBI101.3, and pIG121 vectors. A binary vector is a shuttle vector capable of replicating in *Escherichia coli* and *Agrobacterium*. When a plant is infected with *Agrobacterium* containing a binary vector, DNA corresponding to a region between border sequences (the LB sequence and the RB sequence) present on the vector can be incorporated into nuclear DNA of the plant (EMBO Journal, 10 (3), 697-704, 1991). Meanwhile, a gene can be directly introduced into a plant using a pUC vector. Examples of a pUC vector include pUC18, pUC19, and pUC9. In addition, plant virus vectors, such as cauliflower mosaic virus (CaMV), bean golden mosaic virus (BGMV), and tobacco mosaic virus (TMV), can be used.

In order to facilitate ligation and/or insertion into a vector, the gene expression regulatory DNA and/or the flower-bud-formation-inducing gene can be adequately modified via substitution, insertion, or addition of a restriction enzyme recognition sequence. For insertion into a vector, it is possible to use, for example, a method comprising cleaving purified DNA comprising the gene expression regulatory DNA and the flower-bud-formation-inducing gene with an adequate restriction enzyme and inserting each obtained fragment into the restriction enzyme recognition site or the multicloning site of adequate vector DNA for ligation to the vector.

If necessary, an enhancer, an intron, a poly-A addition signal, a 5'-UTR sequence, a selection marker gene, or the like can be ligated to a site upstream, inside, or downstream of the gene expression regulatory DNA and/or flower-bud-formation-inducing gene in the vector.

An enhancer is used, for example, to improve expression efficiency of the flower-bud-formation-inducing genes. An example thereof is an enhancer region containing a sequence located upstream in a CaMV35S promoter.

A terminator may be a sequence that can terminate transcription of a gene caused by the above promoter. Examples thereof include a nopalin synthetase gene terminator, an octopine synthetase gene terminator, and a CaMV 35S RNA gene terminator.

Examples of a selection marker gene include a hygromycin-resistant gene, a kanamycin-resistant gene, a bialaphos-resistant gene, a blasticidin S-resistant gene, and an acetolactate synthase gene. A selection marker gene may be ligated together with a flower-bud-formation-inducing gene to an identical plasmid as described above for preparation of a recombinant vector. Alternatively, a recombinant vector obtained by ligating a selection marker gene to a plasmid and a recombinant vector obtained by ligating a flower-bud-formation-inducing gene to a plasmid may be separately prepared. When they are separately prepared, a host is cotransfected with both vectors.

A transformant can be produced using the recombinant vector thus prepared.

When a transformed plant is prepared, various methods that have been reported and established can be adequately used. Preferable examples of such methods include an *Agrobacterium* method, a PEG-calcium phosphate method, an electroporation method, a liposome method, a particle gun method, and a microinjection method. The *Agrobacterium* method is carried out with the use of a protoplast, a tissue section, or a plant itself (i.e., an in planta method). When a protoplast is used, such protoplast is subjected to coculture with *Agrobacterium* having a Ti plasmid or fusion with an *Agrobacterium* spheroplast (i.e., a spheroplast method). When a tissue section is used, an aseptic culture leaf section (leaf disc) or calluses of a target plant may be infected with *Agrobacterium*. When an in planta method involving the use of a seed or plant (i.e., a system that does not perform tissue culture with the addition of a plant hormone) is employed, water-absorbing seeds, a young plant (young seedling), a potted plant, and the like may be directly treated with *Agrobacterium*.

Whether or not a DNA comprising the gene expression regulatory DNA and the flower-bud-formation-inducing gene has been incorporated into a plant can be confirmed via PCR, Southern hybridization, Northern hybridization, Western blotting, or other techniques. For example, DNA is prepared from a transformed plant, DNA-specific primers are designed, and PCR is then carried out. Thereafter, an amplification product is subjected to agarose gel electrophoresis, polyacrylamide gel electrophoresis, capillary electrophoresis, or other means, followed by staining with ethidium bromide, SYBR Green liquid, or the like. By detecting an amplification product in the form of a single band, plant transformation can be confirmed. In addition, an amplification product can be detected by PCR using primers preliminarily labeled with a fluorescence dye or the like. Further, the amplified product may be allowed to bind to a solid phase, such as a microplate, and the amplified product may then be detected via, for example, a fluorescence or enzyme reaction.

Examples of plants used for transformation in the present invention include, but are not particularly limited to, plants belonging to the families Gramineae, Solanaceae, Brassicaceae, Leguminosae, Rosaceae, Asteraceae, Liliaceae, Apiaceae, Caryophyllaceae, Cucurbitaceae, Convolvulaceae, and Chenopodiaceae. Preferable examples thereof include plants belonging to the family Gramineae, such as sugarcane, rice, barley, wheat, maize, zoysia, *Sorghum*, millet, Japanese millet, napier grass, and switchgrass.

Examples of plant materials subjected to transformation in the present invention include plant tissue of root, stalk, leaf, seed, embryo, ovule, ovary, shoot apex (a growth point at the tip of a plant bud), anther, pollen, or the like, a section of such a plant tissue, undifferentiated callus, and cultured plant cells such as protoplasts obtained by subjecting the above examples to enzyme treatment for cell wall removal. When an in planta method is employed, in addition, water-absorbing seeds and a whole plant body can be used.

The term "transformed plant" used in the present invention refers to a whole plant body, a plant organ (e.g., a root, stalk, leaf, petal, seed, or fruit), a plant tissue (e.g., epidermis, phloem, parenchyma, xylem, or vascular bundle), or a plant culture cell.

When plant culture cells are used, a plant organ or a plant itself can be regenerated by a known tissue culture method, so as to regenerate a transformed plant from the obtained transformed cells. A person skilled in the art can readily implement such procedure in accordance with a conventional technique for regeneration of a plant from plant cells. For example, a plant can be regenerated from plant cells in the manner described below.

When a plant tissue or protoplast is used as a target plant material for transformation, it is cultured in a sterilized callus formation medium supplemented with an inorganic elements, vitamins, a carbon source, sugar used as an energy source, a plant growth regulator (e.g., a plant hormone such as auxin or cytokinin), and the like for formation of a dedifferentiated callus capable of growing adventitiously (hereinafter referred to as "callus induction"). The thus formed callus is transferred to a fresh medium containing a plant growth regulator such as auxin for further growth (subculture).

Callus induction is carried out on a solid medium such as agar. Subculture is carried out via, for example, liquid culture. In such case, each culture can be carried out efficiently and on a large scale. Subsequently, the callus grown by subculture described above is cultured under adequate conditions for induction of organ redifferentiation (hereinafter referred to as "redifferentiation induction"). This eventually results in the regeneration of a complete plant. Redifferentiation induction can be performed by determining types and amounts of a plant growth regulator, such as auxin or cytokinin, and different components, such as a carbon source, to be added to a medium, and adequately setting light, temperature, and other conditions. Such redifferentiation induction results in formation of an adventitious embryo, root, bud, stalk leaf, or the like, followed by further cultivation for acquisition of a complete plant. Alternatively, a redifferentiated product may be preserved in the state it is in before it becomes a complete plant (e.g., as an encapsulated artificial seed, dry embryo, or lyophilization cell or tissue).

According to the present invention, the term "transformed plant" refers to a "T1 generation plant" obtained as a first generation plant via redifferentiation after transformation. The term also refers to a "T2 generation plant" obtained as a plant of the subsequent generation from seeds of the T1 generation plant and a progeny plant such as a next generation (T3 generation) plant obtained via self-pollination of a flower of a "T2 generation" plant that has been found to be a transgenic plant via, for example, drug selection or Southern analysis.

The thus produced transformed plant expresses the introduced flower-bud-formation-inducing gene specifically in mature leaves.

In the transformed plant according to the present invention, flower bud formation or ear emergence is promoted, and differentiation and/or formation of flower buds or flower organs, ear emergence, and/or flowering take place earlier than the same in wild-type plants. Specifically, the period from sowing to ear emergence and/or flowering of the transformed plant according to the present invention is shorter than that of wild-type plants.

In the transformed plant according to the present invention, also, branching is promoted, and branching takes place earlier and/or the number of branching increases than the same in wild-type plants.

DNA according to the present invention that comprises gene-expression-regulating DNA having activity of promoting gene expression specifically in mature leaves and the flower-bud-formation-inducing gene has a function of promoting ear emergence and/or branching of plants, and in particular, sugarcane plants and plants closely related thereto. DNA according to the present invention is capable of inducing ear emergence in a plant variety that does not usually undergo ear emergence, shortening the period up to ear emergence, shortening the period up to branching, and/or increasing the number of branching. Because of the features as described above, the number of branching capable of ear emergence; that is, the number of effective branching, can be increased in a transformed plant into which the DNA according to the present invention has been introduced. Thus, cross breeding can be efficiently carried out, regardless of the time necessary for ear emergence and the capacity for ear emergence. In addition, a transformed plant into which the DNA according to the present invention has been introduced has a short generation time that is ½ to ⅕, and preferably ⅓, of that of a wild-type plant. This can enhance the efficiency for cross breeding.

EXAMPLES

Hereafter, the present invention is described in greater detail with reference to the examples, although the technical scope of the present invention is not limited to these examples.

Example 1

Cloning of Mature-Leaf-Specific Gene

Total RNA was extracted and purified from mature leaf, young leaf, and stalk tissues of sugarcane (*Saccharum* spp. cv. NiF8) using RNeasy Plant Mini Kits (QIAGEN). A cDNA library was constructed in accordance with a conventional technique and used for gene expression analysis. Gene expression analysis was carried out using a Sugarcane Genome Array (Affimetrix) according to the manufacturer's instructions.

As a result of gene expression analysis, a gene expressed at a particularly high level in mature leaves of *Saccharum* spp. cv. NiF8 was identified and designated as the "ecc0002" gene. The nucleotide sequence of the *Saccharum* spp. cv. NiF8-derived ecc0002 gene is identical to the nucleotide sequence of *Saccharum officinarum*-derived ecc0002 EST shown in FIG. 1. Total RNA was extracted and purified from mature leaves, young leaves, stalk pith, stalk epidermis, roots, and meristem of *Saccharum* spp. cv. NiF8. cDNA was prepared in accordance with a conventional technique. The ecc0002 gene expression level in each tissue was analyzed via a SYBRGreen method using an ABI7500 real-time PCR system (Applied Biosystems).

FIG. 2 shows the results (where the highest gene expression level in mature leaves is designated as 100%). The results revealed that expression of the ecc0002 gene is strongly induced in mature leaves of *Saccharum* spp. cv. NiF8.

Example 2

Acquisition of Mature-Leaf-Specific Promoter

Genomic DNA (approximately 300 ng) was extracted and purified from 0.5 g of mature leaf tissue of sugarcane (*Saccharum* spp. cv. NiF8) using DNeasy Plant Mini Kits (QIAGEN). The gene expression regulatory region located 5'-upstream of the ecc0002 gene was obtained from the above genomic DNA based on the nucleotide sequence of the ecc0002 gene obtained in Example 1 using RightWalk® Kits (BEX Co., Ltd.). An HindIII restriction enzyme recognition sequence (AAGCTT) and a BlnI restriction enzyme recognition sequence (CCTAGG) were used as linker sequences. The former was introduced at the 5'-terminus of the obtained gene expression regulatory region and the latter was introduced on the 3' side of the translation initiation site (ATG) of the ecc0002 gene located at the 3'-terminus of the gene expression regulatory region. Thus, DNA encoding the expression regulatory region of the ecc0002 gene was prepared (FIG. 3) (SEQ ID NO: 5).

The above DNA sequence was analyzed with the use of a conventional promoter analysis tool (BioInformatics and Molecular Analysis Section) (www-bimas.cit.nih.gov/molbio/proscan/). As a result, a region that serves as a promoter was presumed to exist in the region comprising the 875th to 1125th nucleotides in SEQ ID NO: 5.

Example 3

Construction of β-Glucuronidase Gene Expression Vector

Figure 5:
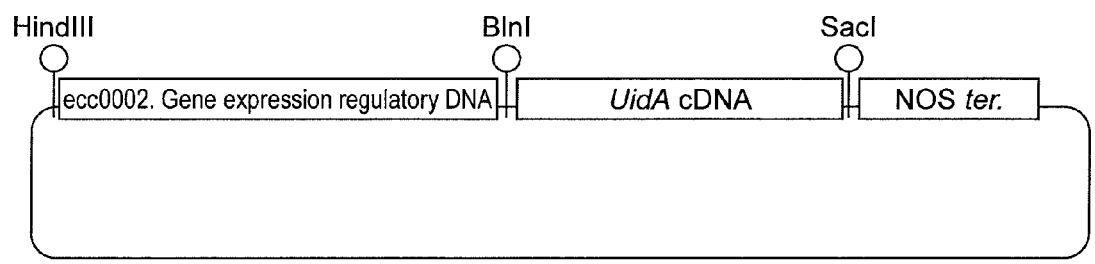
FIG. 5 schematically shows a gene expression vector containing the gene expression regulatory region of the ecc0002 gene and the β-glucuronidase gene ligated to each other.

A gene expression vector comprising DNA encoding the gene expression regulatory region obtained in Example 2 ligated to UidA cDNA encoding the β-glucuronidase (GUS) gene was constructed. A plant transformation vector (pBII221) was used for the gene expression vector. DNA encoding a gene expression regulatory region was ligated to UidA cDNA in such a manner that the ATG sequence encoding the first methionine located on the 5'-terminal side of UidA cDNA would align with the ATG sequence encoding the first methionine of the ecc0002 gene located on the 3'-terminal side of the DNA encoding a gene expression regulatory region (translational fusion type). FIG. 5 schematically shows the gene expression vector.

Example 4

Production of GUS Expression Gene Recombinant Plant

The gene expression vector produced in Example 3 was introduced into a host plant (*Saccharum* spp. cv. NiF8) by the *Agrobacterium* method. Thus, a transgenic sugarcane in which GUS gene expression was regulated by the expression regulatory DNA of the ecc0002 gene was produced. Total RNA was extracted and purified from mature leaves, young leaves, stalk pith, stalk epidermis, roots, and meristem of the transgenic sugarcane. cDNA was prepared in accordance with a conventional technique. The GUS gene expression level in each tissue was analyzed by a SYBR-Green method using an ABI7500 real-time PCR system (Applied Biosystems).

For comparison, the GUS gene expression levels in mature leaves and young leaves of the transgenic sugarcane in which the GUS gene expression was regulated by a cauliflower mosaic virus (CaMV) 35S promoter and the GUS expression level in the meristem of non-transgenic sugarcane (control) were analyzed in the above manner.

Figure 6:
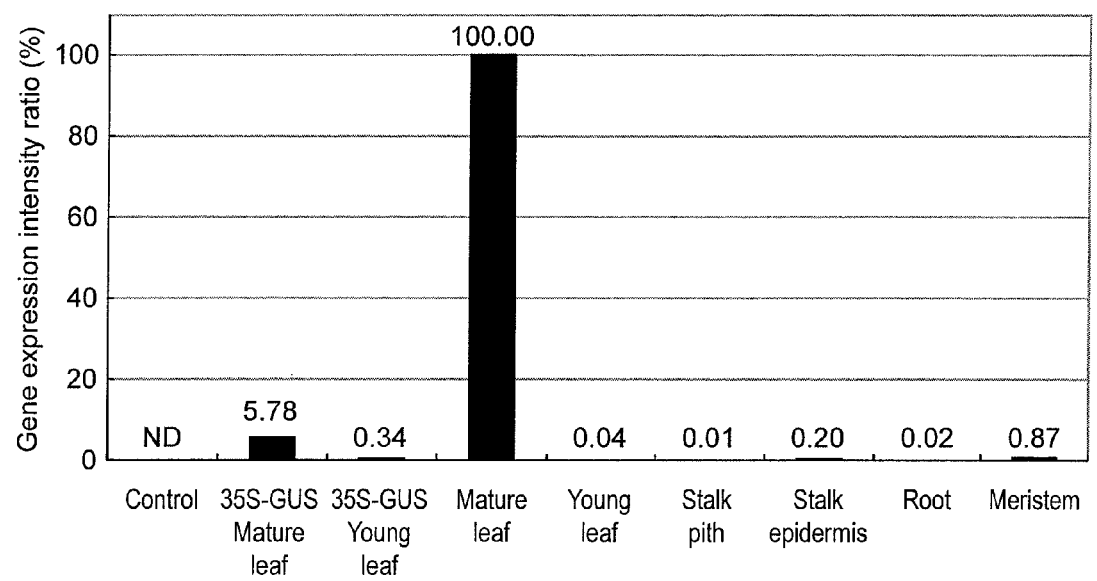
FIG. 6 shows results of GUS gene expression level analysis for individual tissues of a transgenic sugarcane in which β-glucuronidase gene expression is regulated by the expression regulatory DNA of the ecc0002 gene. The highest expression level confirmed for mature leaves of the transgenic sugarcane is designated as 100%.

FIG. 6 shows the results. The expression levels of the individual tissues are expressed in relative values with reference to the highest GUS gene expression level confirmed in tissues of mature leaves among the analyzed tissues of transgenic sugarcane (in which GUS gene expression was regulated by the ecc0002 gene expression regulatory DNA), which was designated as 100%.

The above results revealed that the ecc0002 gene expression regulatory DNA can induce gene expression specifically in mature leaves to an extent approximately 17 times greater than the GUS gene expression level regulated by a CaMV35S promoter.

Example 5

Construction of Rice Hd3a Gene Expression Vector

Figure 8:
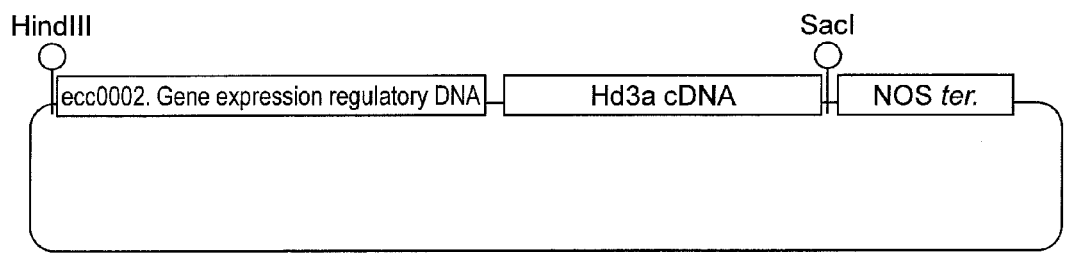
FIG. 8 schematically shows a gene expression vector containing the gene expression regulatory region of the ecc0002 gene and the rice Hd3a gene ligated to each other.

A gene expression vector comprising DNA encoding the gene expression regulatory region obtained in Example 2 ligated to cDNA encoding rice Hd3a (referred to as "Hd3a cDNA") was constructed. A plant transformation vector (pIG121-Hm) was used for the gene expression vector. DNA encoding the gene expression regulatory region was ligated to Hd3a cDNA in a manner such that the ATG sequence encoding the first methionine located on the 5'-terminal side of Hd3a cDNA would align with the ATG sequence encoding the first methionine of the ecc0002 gene, located on the 3'-terminal side of the DNA encoding the gene expression regulatory region (translational fusion type). FIG. 7 shows the sequence comprising DNA encoding the gene expression regulatory region ligated to Hd3a cDNA (SEQ ID NO: 3). Also, FIG. 8 schematically shows the gene expression vector.

Example 6

Production of Transgenic Plant Expressing Rice Hd3a Gene

The gene expression vector produced in Example 5 was introduced into a host plant (*Saccharum* spp. cv. NiF8) via the *Agrobacterium* method. Thus, a transgenic sugarcane line in which rice Hd3a gene expression would be regulated by the expression regulatory DNA of the ecc0002 gene was produced.

For comparison, a wild-type sugarcane and a transgenic sugarcane in which rice Hd3a gene expression would be regulated by a CaMV 35S promoter were prepared and used.

Total RNAs were extracted and purified from calluses, redifferentiated tissues, and mature leaves of transgenic sugarcanes, cDNAs were prepared in accordance with a conventional technique, and the rice Hd3a gene expression levels in tissues were analyzed via the SYBR Green method using the ABI7500 Real-Time PCR apparatus (Applied BioSystems). It should be noted that the term "redifferentiated tissue" refers to tissue obtained by inducing calluses to redifferentiate, but the term does not refer to a tissue or organ of a plant that has been completely regenerated. The actin gene expression level was analyzed in the same manner as that used for the internal standard.

Figure 9:
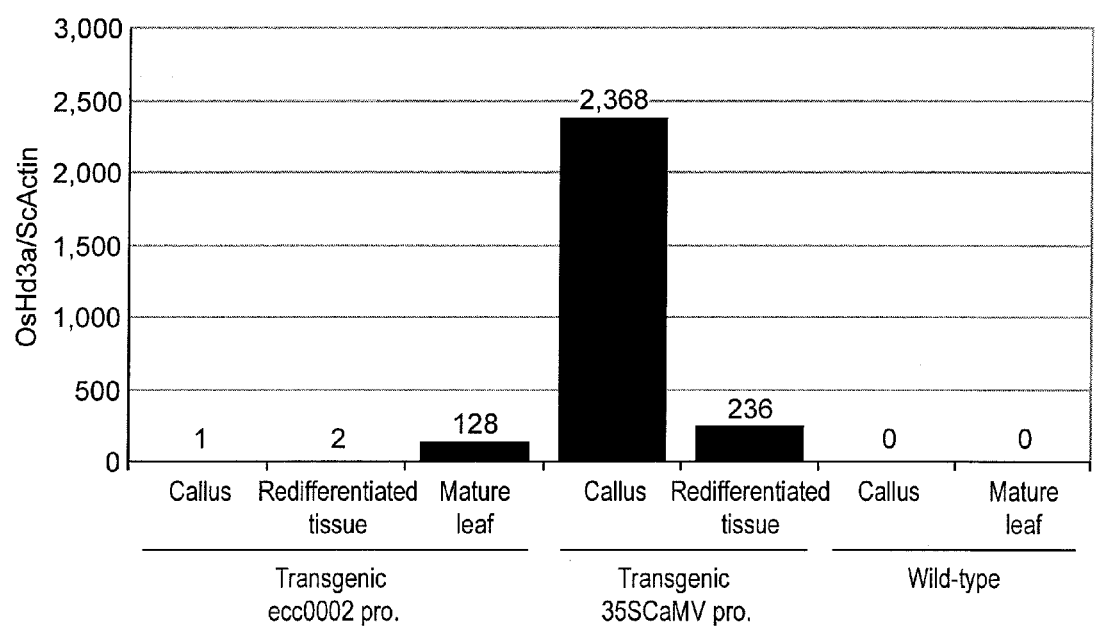
FIG. 9 shows the results of rice Hd3a gene expression level analysis for individual tissues of a transgenic sugarcane in which rice Hd3a gene expression is regulated by expression regulatory DNA of the ecc0002 gene, a transgenic sugarcane in which rice Hd3a gene expression is regulated by the CaMV 35S promoter, and a wild-type sugarcane. In the table, "transgenic ecc0002 pro." refers to a transgenic sugarcane in which rice Hd3a gene expression is regulated by the gene expression regulatory region of the ecc0002 gene, and "transgenic 35SCaMV pro." refers to a transgenic sugarcane in which rice Hd3a gene expression is regulated by the CaMV 35S promoter.

The results are shown in FIG. 9.

The rice Hd3a genes that had been introduced into transgenic sugarcane lines in which rice Hd3a gene expression would be regulated by expression regulatory DNA of the ecc0002 gene were expressed specifically in the redifferentiated mature leaf tissues.

In contrast, transgenic sugarcane lines in which rice Hd3a gene expression would be regulated by the CaMV 35S promoter were introduced into a medium for redifferentiation of recombinant calluses. Such calluses turned brown in approximately 2 weeks, and all the recombinant calluses died thereafter. Unlike other plants such as *Oryza sativa* and *Arabidopsis thaliana*, the Hd3a gene was found to have lethal effects at the stage of sugarcane redifferentiation.

Example 7

Ability to Induce Ear Emergence and Branching in Transgenic Plant Expressing Rice Hd3a Gene The ability to induce ear emergence and branching in a transgenic plant expressing the rice Hd3a gene prepared in Example 6 was investigated.

Figure 10:
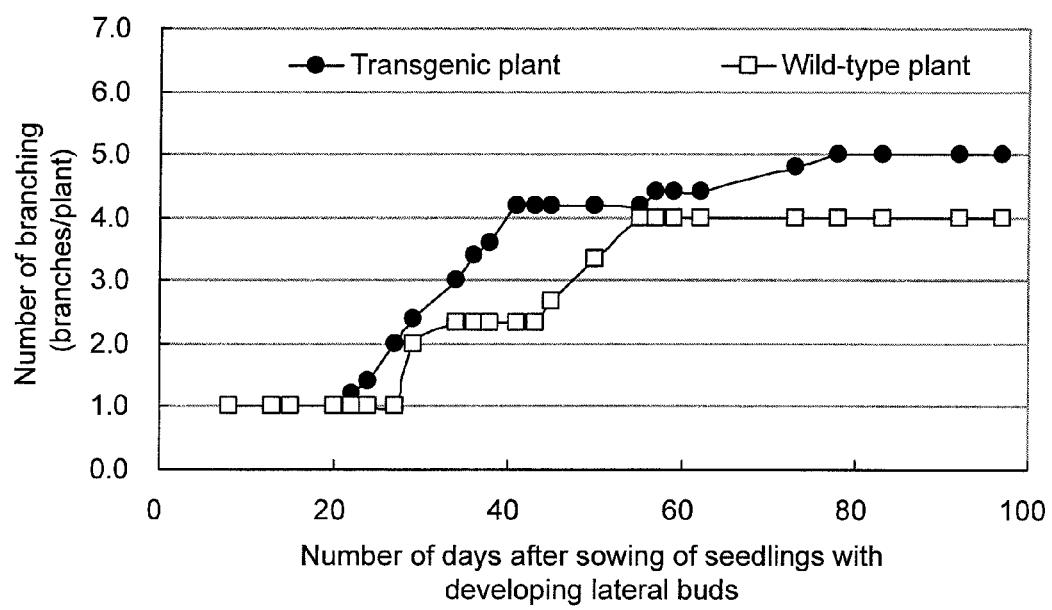
FIG. 10 shows the results of analysis of the ability to induce branching of a transgenic sugarcane in which rice Hd3a gene expression is regulated by expression regulatory DNA of the ecc0002 gene. The number of branching is the average of the number of branching for transgenic sugarcanes (n=5) and that for wild-type sugarcanes (n=3).
Figure 11:
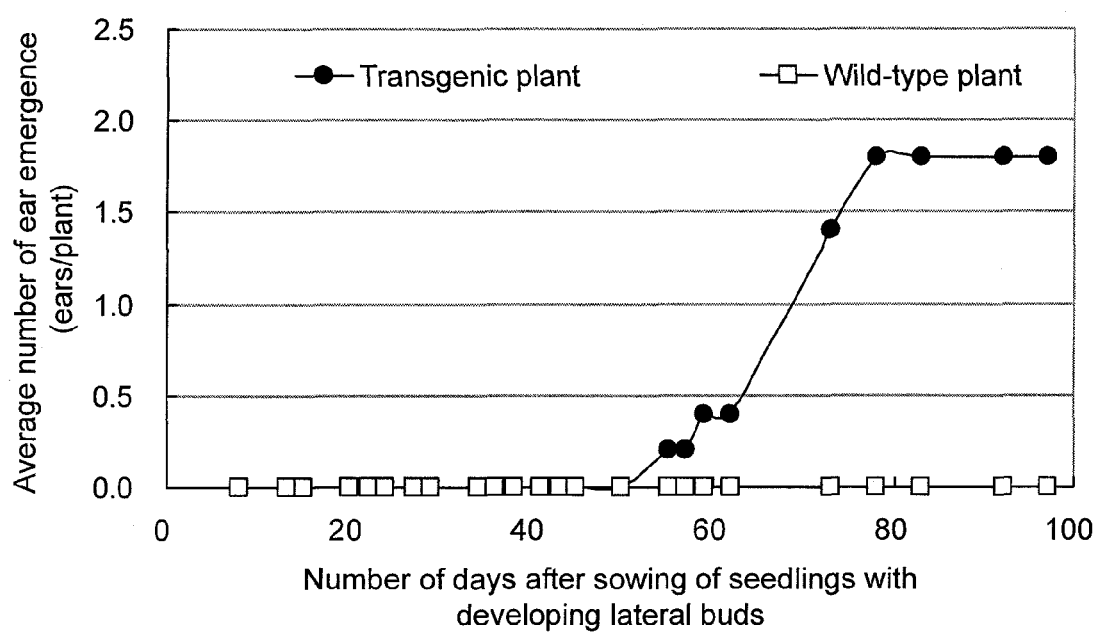
FIG. 11 shows the results of analysis of the ability to induce ear emergence of a transgenic sugarcane in which rice Hd3a gene expression is regulated by expression regulatory DNA of the ecc0002 gene. The number of ear emergence is the average of the number of ear emergence for transgenic sugarcanes (n=5) and that for wild-type sugarcanes (n=3).

The results are shown in FIGS. 10 and 11.

Concerning the transgenic plant expressing the rice Hd3a gene, branching was observed at the initial growth stage, which is approximately 20 days after sowing of seedlings prepared from developing lateral buds (FIG. 10), and ear emergence was observed approximately 2 months after sowing of seedlings prepared from developing lateral buds (FIG. 11).

In contrast, the period from sowing of the seedlings prepared from developing lateral buds to observation of branching for wild-type plants was longer than that for the transgenic plant using the rice Hd3a gene (FIG. 10), and ear emergence had not been observed 3 months after sowing of the seedlings prepared from developing lateral buds (FIG. 11).

The results demonstrate that transgenic sugarcane plants in which rice Hd3a gene expression is regulated by expression regulatory DNA of the ecc0002 gene can be sufficiently induced to undergo branching and ear emergence. In addition, such transgenic sugarcane plants are capable of further ear emergence from branched stalks, which in turn enables maintenance of ear-emerging stalks for a long period of time (i.e., several months).

INDUSTRIAL APPLICABILITY

According to the present invention, ear emergence and/or branching can be promoted in plants, and, in particular, sugarcane plants and plants closely related thereto. This enables efficient cross breeding, regardless of the time necessary for ear emergence and the capacity for ear emergence, and it also realizes a shorter generation time of a plant. Thus, the efficiency of cross breeding can be remarkably improved. Accordingly, the present invention is expected to make a remarkable contribution to cross breeding of plants, and, in particular, sugarcane plants and plants closely related thereto.

All publications, patents, and patent applications cited herein are incorporated herein by reference in their entirety.

The invention claimed is:

1. DNA consisting of the nucleotide sequence as shown in SEQ ID NO: 1 operably linked to a nucleotide sequence encoding a polypeptide consisting of the amino acid sequence as shown in SEQ ID NO: 7,
wherein, the DNA drive expression of the nucleotide sequence encoding the polypeptide specifically in a mature-leaf-specific manner and promotes flower bud formation or ear emergence and/or branching of a plant.

2. A recombinant vector comprising the DNA according to claim 1.

3. A transformed plant into which the DNA according to claim 1 is introduced.

4. The transformed plant according to claim 3, which belongs to the family Gramineae.

5. The transformed plant according to claim 4, which belongs to the genus *Saccharum*, *Sorghum*, or *Miscanthus*.

6. A transformed plant into which the recombinant vector according to claim 2 is introduced.

* * * * *

SEQUENCE LISTING

```
<160> NUMBER OF SEQ ID NOS: 7

<210> SEQ ID NO 1
<211> LENGTH: 1536
<212> TYPE: DNA
<213> ORGANISM: Saccharum spp. cv. NiF8

<400> SEQUENCE: 1
taggagatgc ggtgtggtac taaatgcaag gtccaaattc aatgctttt ccatgtttct      60 ttgaaacgca atgccacatc tttctttaaa gtaagaactg aggggtccca tgtttctttt     120 tgcactttc acaagaatgt acaactgaaa atatcatgaa acatcattac cctctttata     180
tgcgtcgtca tctattcacc taaactcact gataggatta atgcacttca gtacactcat     240
acgtgacaac tactgttttt gaaagtgaac atttgtagtg ctactatttg catgtatggg     300
aaattgggaa ttctttcttg ccatggctga tccagatctc gacctgcttg atctaatgca     360
aacatgcatg ttgatagcaa gctgaggatc tagagatata aggtgttagg agatgcggtg     420
tggtactaaa tgcaaggtca aaattccatg cttttccat gctcaattac ctagcatttc     480 ctaatttta attgtgataa ctaatgcatc gagccatata taattcagta aatatgtata     540
tttaagcata tatatatata tacagtttac atttctaatt cttctttttt tgtgtggagg     600
tccgcgacga tgcaagttgc tcccaaccca aattaatcca cctctcttaa atccgcagat     660
cttcaccacc agcagctaca catcgtattg tgtcggcttg accgcatgtg cgcgctgggt     720
tttggcagcg cctgaatgca gtacagccac ctgtatggtg cccttggtag agtaacaccc     780
ttatccctac ggcagccatg tataacccctt atccctacgg cagccatgta ttgtagccca     840
tcttcttaac cacaagttca tttaaattt ccggccggtc tcttgaggaa atcaaatttt     900
attttcacaa tttatatgga tataggataa tctatgttcc taacagtggc taacaggctc     960
cctctcctcc acatacatcg cgtgcaagca ttcctccaaa ctcttccgat cccccgaatc    1020
cagccttgac tgcaaacaga cgcccctctc cacatcctgc acaccatca gccaacgaa     1080 taacagaaga aggcgagtga gcagtgacaa agcacgtcaa cagcagcgag ccaagccaaa    1140
atggagccag gagcaagccg cggccgcagc tctcccggtc ccccttgcgg ttaccgctag    1200
caaacgcccc tctccacatc ctgcaacaca aggaggcaag tgcgcagtga caaagtacgt    1260
ccacagcagc gagccaagcc aaaaggagct cagccacagc cgcagctctc ggctaccgtt    1320
accgccgatc acatgcatgc ctttccaaac gccaaggcc gcgcaatccc gtgcacaccg    1380
accacacact cgccaactcc ccatccctat ttgaagccac cggcccgcgc actgcattga    1440
```

```
tcaactcgca gcagtagagc agcacgagca acacgccgcg ccgctccaac catctcagct    1500
tcgcgcttcc cgcgccccgc cgccgcgccc gccatg                              1536

<210> SEQ ID NO 2
<211> LENGTH: 540
<212> TYPE: DNA
<213> ORGANISM: Oryza sativa Japonica Group

<400> SEQUENCE: 2
atggccggaa gtggcaggga cagggaccct cttgtggttg gtagggttgt gggtgatgtg      60
ctggacgcgt tcgtccggag caccaacctc aaggtcacct atggctccaa gaccgtgtcc     120
aatggctgcg agctcaagcc gtccatggtc acccaccagc ctagggtcga ggtcggcggc     180
aatgacatga ggacattcta caccctttgtg atggtagacc cagatgcacc aagcccaagt    240
gaccctaacc ttagggagta tctacattgg ttggtcactg atattcctgg tactactgca    300
gcgtcatttg gcaagaggt gatgtgctac gagagcccaa ggccaaccat ggggatccac      360
cggctggtgt tcgtgctgtt ccagcagctg ggcgtcaga cagtgtacgc gcccgggtgg      420
cgtcagaact tcaacaccaa ggacttcgcc gagctctaca acctcggctc gccggtcgcc    480
gccgtctact tcaactgcca gcgcgaggca ggctccggcg caggagggt ctaccccctag    540

<210> SEQ ID NO 3
<211> LENGTH: 2079
<212> TYPE: DNA
<213> ORGANISM: Artificial Sequence
<220> FEATURE:
<223> OTHER INFORMATION: Synthetic polynucleotide

<400> SEQUENCE: 3
aagctttagg agatgcggtg tggtactaaa tgcaaggtcc aaattcaatg cttttttccat    60 gtttctttga aacgcaatgc cacatctttc tttaaagtaa gaactgaggg gtcccatgtt    120 tcttttgca cttttcacaa gaatgtacaa ctgaaaatat catgaaacat cattaccctc    180
tttatatgcg tcgtcatcta ttcacctaaa ctcactgata ggattgatgc acttcagtac    240
actcatacgt gacaactact gtttttgaaa gtgaacattt gtagtgctac tatttgcatg    300
tatgggaaat tgggaattct ttcttgccat ggctgatcca gatctcgacc tgcttgatct    360
aatgcaaaca tgcatgttga tagcaagctg aggatctaga gatataaggt gttaggagat    420
gcggtgtggt actaaatgca aggtcaaaat tccatgcttt ttccatgctc aattacctag    480
catttcctaa ttttttaattg tgataactaa tgcatcgagc catatataat tcagtaaata    540
tgtatattta agcatatata tatatataca gtttacattt ctaattcttc tttttttgtg    600
tggaggtccg cgacgatgca agttgctccc aacccaaatt aatccacctc tcttaaatcc    660
gcagatcttc accaccagca gctacacatc gtattgtgtc ggcttgaccg catgtgcgcg    720
ctgggttttg gcagcgcctg aatgcagtac agccacctgt atggtgccct ggtagagta    780 acacccttat ccctacggca gccatgtata acccttatcc ctacggcagc catgtattgt    840
agcccatctt cttaaccaca agttcatttt aaatttccgg ccggtctctt gaggaaatca    900
aattttattt tcacaattta tatggatata ggataatcta tgttcctaac agtggctaac    960
aggctccctc tcctccacat acatcgcgtg caagcattcc tccaaactct tccgatcccc    1020
cgaatccagc cttgactgca aacagacgcc cctctccaca tcctgcacac ccatcagcca    1080
acggaataac agaagaaggc gagtgagcag tgacaaagca cgtcaacagc agcgagccaa    1140
gccaaaatgg agccaggagc aagccgcggc cgcagctctc ccggtccccc ttgcggttac    1200
```

| | |
|---|---|
| cgctagcaaa cgcccctctc cacatcctgc aacacaagga ggcaagtgcg cagtgacaaa | 1260 |
| gtacgtccac agcagcgagc caagccaaaa ggagctcagc cacagccgca gctctcggct | 1320 |
| accgttaccg ccgatcacat gcatgccttt ccaaacgcca agggccgcgc aatcccgtgc | 1380 |
| acaccgacca cacactcgcc aactccccat ccctatttga agccaccggc ccgcgcactg | 1440 |
| cattgatcaa ctcgcagcag tagagcagca cgagcaacac gccgcgccgc tccaaccatc | 1500 |
| tcagcttcgc gcttcccgcg ccccgccgcc gcgcccgcca tggccggaag tggcagggac | 1560 |
| agggaccctc ttgtggttgg tagggttgtg ggtgatgtgc tggacgcgtt cgtccggagc | 1620 |
| accaacctca aggtcaccta tggctccaag accgtgtcca atggctgcga gctcaagccg | 1680 |
| tccatggtca cccaccagcc tagggtcgag gtcggcggca atgacatgag gacattctac | 1740 |
| acccttgtga tggtagaccc agatgcacca agcccaagtg accctaacct tagggagtat | 1800 |
| ctacattggt tggtcactga tattcctggt actactgcag cgtcatttgg gcaagaggtg | 1860 |
| atgtgctacg agagcccaag gccaaccatg gggatccacc ggctggtgtt cgtgctgttc | 1920 |
| cagcagctgg ggcgtcagac agtgtacgcg cccgggtggc gtcagaactt caacaccaag | 1980 |
| gacttcgccg agctctacaa cctcggctcg ccggtcgccg ccgtctactt caactgccag | 2040 |
| cgcgaggcag gctccggcgg caggagggtc taccccctag | 2079 |

<210> SEQ ID NO 4
<211> LENGTH: 3389
<212> TYPE: DNA
<213> ORGANISM: Saccharum officinarum

<400> SEQUENCE: 4

| | |
|---|---|
| atcaaactcg cagcagtaga gcagcacgag caacacgccg cgccgctcca accatctcag | 60 |
| cttcgcgctt cccgcgcccc gccgccgcgc ccgccatggc gtccgagcgg caccactcca | 120 |
| tcgacgcgca gctccgtgcc ctggcccccg gcaaggtctc cgaggagctc atccagtacg | 180 |
| acgccctgct cgccgaccgt ttcctcgaca tcctccagga cctccatggc cctagccttc | 240 |
| gcgaatttgt ccaggagtgc tacgaggtgt cggccgatta cgagggcaag aaggacacgt | 300 |
| cgaagctggg cgagctgggc accaagctca cggggctggc gcccgccgac gccatcctgg | 360 |
| tggcgagctc catcctgcac atgctcaacc tggccaacct ggccgaggaa gtggagctgg | 420 |
| cgcaccgccg ccggaacagc aagctcaagc acggggactt ctccgacgag ggctccgcca | 480 |
| ccaccgagtc ggacatcgag gagacgctca gcgcctcgt gtcgctgggc aagacccccg | 540 |
| aggaggtgtt cgaggcgctc aagaaccaga gcgtcgacct cgtcttcacc gcgcacccca | 600 |
| cgcagtccgc caggaggtcg ctcctgcaga aaaacgccag gatccggaat tgtctgacgc | 660 |
| agctgagtgc caaggacgtc acggacacg acaagaagga gctcgacgag gctctgcaga | 720 |
| gagagatcca agcagctttc agaactgatg agatccggag agcacaaccc accccacagg | 780 |
| atgaaatgcg ctatgggatg agctacatcc atgaaactgt atggaagggt gtgcctaagt | 840 |
| ttttgcgccg tgtggataca gccctgaaga atatcggcat caatcagcgc ttccctaca | 900 |
| atgttcctct cattaagttc tggtcttgga tgggtggtga ccgtgatgga atccaagag | 960 |
| taactccgga ggtgacaaga gaagtatgct tgctgtccag aatgacggct gcaaacttgt | 1020 |
| acatcgatca ggtcgaagac ctgatgtttg agctctctat gtggcgctgc aatgatgaac | 1080 |
| ttcgtgctcg agccgaagaa gtccagagta ctccagcttc aaagaaagtt accaagtatt | 1140 |
| acatagaatt ctggaagcaa attcctccaa acgagcccta ccgggtgata cttggtgctg | 1200 |
| taagggacaa gttatacaac acacgcgagc gtgcacgcca tctgctggca actggatttt | 1260 |

```
ctgaaatttc tgtggactcg gtatttacca atatcgaaga gttccttgag ccccttgagc    1320
tatgctacaa atccctgtgt gactgcggcg acaaggccat cgcggacggg agcctcctgg    1380
acctcctgcg ccaggtgttc acgttcgggc tctccctggt gaagttggac atccgtcagg    1440
agtcggagcg gcacaccgac gtgatcgacg ccatcaccac gtaccttggc atcgggtcgt    1500
accgctcgtg gcccgaggac aagcggatgg agtggctggt gtcggagctg aaaggcaagc    1560
ggccgctgct gccccggac cttcccatga ccgaggagat cgccgacgtc atcggggcga    1620
tgcacgtcct cgcggagctc ccgtcggaca gcttcggccc ctacatcatc tccatgtgca    1680 cagcccctc cgacgtgctc gccgtggagc tcctgcagcg cgagtgtggc attcgccaga    1740
cgctgcccgt ggtgccgctg ctcgagaggc tggccgacct gcaggcggcg cccgcgtccg    1800
tggagcggct cttctccact gactggtact cgaccacat caagggcaag cagcaggtga    1860
tggtcgggta ctccgactcc ggcaaggacg ccggccgcct gtccgcggcg tggcagctgt    1920
acgtggcgca ggaggagatg gccaaggtgg ccaagaaata cggcgtgaag ctgaccttgt    1980
tccacgggcg cggcggcacc gtgggcaggg gtggcgggcc gacgcacctg gccatcctgt    2040
cccagccgcc ggacaccatc aacgggtcaa tccgcgtgac ggtgcagggc gaggtcatcg    2100
agttcatgtt cggggaggat cacctgtgct tccagtctct gcagcgcttc acggccgcca    2160
cgctggagca cggcatgcac ccgccggtgt ctcccaagcc cgagtggcgc aagctcatgg    2220
aggagatggc agtcgtggcc acggaggagt accgctccgt cgtcgtcaag gagccgagat    2280
tcgtcgagta cttcagatcg gctacccctg agactgagta cgggaagatg aacatcggca    2340
gccggccagc caagaggaag ccgggcggcg gcatcaccac cctgcgcgcc atcccctgga    2400
tcttctcgtg gacccagacg aggttccacc tccccgtgtg gctgggagtc ggcgccgcct    2460
tcaagtgggc catcgacaag gacatcaaga acttccagaa gctcaaagag atgtacaacg    2520
agtggccatt cttcagggtc accctggacc tgctggagat ggttttcgcc aagggagatc    2580
ctggcattgc cggcttgtat gacttgctgc ttgtcgccga cgatctcaag ccctttggga    2640
agcagctcag ggacaaatac gtggagacag agaagcttct cctacagatc gctgggcaca    2700
aggatattct tgaaggcgat ccttacctga agcaggggc gcggctacgc aatccctaca    2760
tcaccaccct gaacgtgttg caggcctaca cgctgaagcg gataagggat ccgagcttca    2820
aggtgacgcc gcagccgccg ctgtccaagg agttcgccga cgagaacaag cccgccggac    2880
tggtgaagct gaacccggcg agcgagtacc cgcccgggct ggaagacacg ctcatcctca    2940
ccatgaaagg tatcgccgcc ggcatgcaga acaccggcta ggccgcttcc cttcactcac    3000
ctgcagagta ctgcacggca ataataatca gcttccggat ggtgtcgttt tgtcagtttt    3060
ggatggaaat gctgaaaact gacaccttct gttttcacta tgtttatgtt tatgtaattt    3120
cctcggcttt ggcctctta tattttcact cttgttgtga agtccaagtg gaaaaatctt    3180
ggcatcttaa acatattgta ataatgaaca tcatacaatc tacaaattta ctattttgta    3240
ttaatctatc tggcagggaa aatgtcactt tatatcccag cccattggat ggactttttt    3300
accatgatgc tagttcaacc atcctctttt gattgtgcta acaatttct gaaatcaaat    3360 gcctggcaat atatgttacc ggttgaatc                                      3389
```

<210> SEQ ID NO 5
<211> LENGTH: 1548
<212> TYPE: DNA
<213> ORGANISM: Artificial Sequence
<220> FEATURE:
<223> OTHER INFORMATION: Synthetic polynucleotide

```
<400> SEQUENCE: 5
aagctttagg agatgcggtg tggtactaaa tgcaaggtcc aaattcaatg cttttttccat    60 gtttctttga aacgcaatgc cacatctttc tttaaagtaa aactgagggg gtcccatgtt   120 tcttttttgca cttttcacaa gaatgtacaa ctgaaaatat catgaaacat cattaccctc   180
tttatatgcg tcgtcatcta ttcacctaaa ctcactgata ggattgatgc acttcagtac   240
actcatacgt gacaactact gttttttgaaa gtgaacattt gtagtgctac tatttgcatg   300
tatgggaaat tgggaattct ttcttgccat ggctgatcca gatctcgacc tgcttgatct   360
aatgcaaaca tgcatgttga tagcaagctg aggatctaga gatataaggt gttaggagat   420
gcggtgtggt actaaatgca aggtcaaaat tccatgcttt ttccatgctc aattacctag   480
catttcctaa ttttttaattg tgataactaa tgcatcgagc catatataat tcagtaaata   540
tgtatattta agcatatata tatatataca gtttacattt ctaattcttc ttttttttgtg   600 tggaggtccg cgacgatgca agttgctccc aacccaaatt aatccacctc tcttaaatcc   660
gcagatcttc accaccagca gctacacatc gtattgtgtc ggcttgaccg catgtgcgcg   720
ctgggttttg gcagcgcctg aatgcagtac agccacctgt atggtgccct tggtagagta   780
acacccttat ccctacggca gccatgtata acccttatcc ctacggcagc catgtattgt   840
agcccatctt cttaaccaca agttcatttt aaatttccgg ccggtctctt gaggaaatca   900 aatttttattt tcacaattta tatggatata ggataatcta tgttcctaac agtggctaac   960
aggctccctc tcctccacat acatcgcgtg caagcattcc tccaaactct tccgatcccc  1020
cgaatccagc cttgactgca aacagacgcc cctctccaca tcctgcacac ccatcagcca  1080
acggaataac agaagaaggc gagtgagcag tgacaaagca cgtcaacagc agcgagccaa  1140
gccaaaatgg agccaggagc aagccgcggc cgcagctctc ccggtccccc ttgcggttac  1200
cgctagcaaa cgcccctctc cacatcctgc aacacaagga ggcaagtgcg cagtgacaaa  1260
gtacgtccac agcagcgagc caagccaaaa ggagctcagc cacagccgca gctctcggct  1320
accgttaccg ccgatcacat gcatgccttt ccaaacgcca agggccgcgc aatcccgtgc  1380
acaccgacca cacactcgcc aactccccat ccctatttga agccaccggc ccgcgcactg  1440
cattgatcaa ctcgcagcag tagagcagca cgagcaacac gccgcgccgc tccaaccatc  1500
tcagcttcgc gcttcccgcg ccccgccgcc gcgcccgcca tgcctagg                1548

<210> SEQ ID NO 6
<211> LENGTH: 847
<212> TYPE: DNA
<213> ORGANISM: Oryza sativa Japonica Group

<400> SEQUENCE: 6
tgcaccacac acagttcagc tagcagatca cctagctaga tagctgcctc tatcacagta    60
tatttgctcc ctgcaacttg ctgctgctgc aatagctagc agctgcagct agtaagcaaa   120
actataaacc ttcagggttt tttgcaagat cgatggccgg aagtggcagg gacagggacc   180
ctcttgtggt tggtagggtt gtgggtgatg tgctggacgc gttcgtccgg agcaccaacc   240
tcaaggtcac ctatggctcc aagaccgtgt ccaatggctg cgagctcaag ccgtccatgg   300
tcacccacca gcctagggtc gaggtcggcg gcaatgacat gaggacattc tacacccttg   360
tgatggtaga cccagatgca ccaagcccaa gtgaccctaa ccttagggag tatctacatt   420
ggttggtcac tgatattcct ggtactactg cagcgtcatt tgggcaagag gtgatgtgct   480
acgagagccc aaggccaacc atggggatcc accggctggt gttcgtgctg ttccagcagc   540
```

```
tggggcgtca gacagtgtac gcgcccgggt ggcgtcagaa cttcaacacc aaggacttcg    600
ccgagctcta caacctcggc tcgccggtcg ccgccgtcta cttcaactgc cagcgcgagg    660
caggctccgg cggcaggagg gtctacccct agctaacgat gatcccgatc gatctgctgc    720
atgctcacta tcatcatcca gcatgctata cattgcaggt tcagacaatt gaaatgattc    780
tcgacacaca acatatatat gatggtgtaa ttaattatgc aattaaatag ctgagcaagg    840
ctaaggt                                                              847

<210> SEQ ID NO 7
<211> LENGTH: 179
<212> TYPE: PRT
<213> ORGANISM: Oryza sativa Japonica Group

<400> SEQUENCE: 7

Met Ala Gly Ser Gly Arg Asp Arg Asp Pro Leu Val Val Gly Arg Val
1               5                   10                  15

Val Gly Asp Val Leu Asp Ala Phe Val Arg Ser Thr Asn Leu Lys Val
            20                  25                  30

Thr Tyr Gly Ser Lys Thr Val Ser Asn Gly Cys Glu Leu Lys Pro Ser
        35                  40                  45

Met Val Thr His Gln Pro Arg Val Glu Val Gly Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
            100                 105                 110

Pro Arg Pro Thr Met Gly Ile His Arg Leu Val Phe Val Leu Phe Gln
        115                 120                 125

Gln Leu Gly Arg Gln Thr Val Tyr Ala Pro Gly Trp Arg Gln Asn Phe
    130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Pro
```